US012588966B2

(12) United States Patent
Flatt et al.

(10) Patent No.: US 12,588,966 B2
(45) Date of Patent: Mar. 31, 2026

(54) ROBOTIC SURGICAL SYSTEM WITH ILLUMINATION DEVICE TO INDICATE MOUNTING ASSEMBLY INSTALLATION CONDITION

(71) Applicant: MAKO Surgical Corp., Weston, FL (US)

(72) Inventors: James E. Flatt, Kalamazoo, MI (US); Robert Dodde, Portage, MI (US); Jonathan Boyer, Galesburg, MI (US); Larry Douglas O'Cull, Westfield, IN (US); Victor Soto, Coral Gables, FL (US); Christopher Wayne Jones, Kokomo, IN (US)

(73) Assignee: MAKO Surgical Corp., Weston, FL (US)

( * ) Notice: Subject to any disclaimer, the term of this patent is extended or adjusted under 35 U.S.C. 154(b) by 0 days.

(21) Appl. No.: 18/788,726

(22) Filed: Jul. 30, 2024

(65) Prior Publication Data

US 2025/0032202 A1     Jan. 30, 2025

Related U.S. Application Data

(63) Continuation of application No. 18/372,721, filed on Sep. 26, 2023, now Pat. No. 12,082,895, which is a
(Continued)

(51) Int. Cl.
*A61B 46/00*        (2016.01)
*A61B 46/23*        (2016.01)
(Continued)

(52) U.S. Cl.
CPC .............. *A61B 46/00* (2016.02); *A61B 46/23* (2016.02); *A61B 90/50* (2016.02); *A61B 2017/00477* (2013.01); *A61B 2560/04* (2013.01)

(58) Field of Classification Search
CPC ......... A61B 46/00; A61B 46/01; A61B 46/23; A61B 2017/0046; A61B 2017/00057
See application file for complete search history.

(56) References Cited

U.S. PATENT DOCUMENTS

| | | | |
|---|---|---|---|
| 3,005,537 | A | 10/1961 | Schmeck et al. |
| 3,005,570 | A | 10/1961 | Manlaz |

(Continued)

FOREIGN PATENT DOCUMENTS

| | | |
|---|---|---|
| AU | 754882 B2 | 11/2002 |
| DE | 102012008535 A1 | 10/2013 |

(Continued)

OTHER PUBLICATIONS

Bateman, D.A., "Adjustable Mirror Mount Design Using Kinematic Principles", Royal Aircraft Establishment, Technical Report No. 66349, Nov. 1966, U.D.C. No. 621.3-21: 531.1: 681.4,. 28 pages.

(Continued)

*Primary Examiner* — Bobby Rushing, Jr.
(74) *Attorney, Agent, or Firm* — Howard & Howard Attorneys PLLC

(57)                    ABSTRACT

Surgical systems and methods involve a robotic arm with a first mounting portion that releasably receives a sterile barrier assembly and a second mounting portion associated with a surgical component. An illumination device is coupled to the robotic arm. Controller(s) detect, using one or more sensors, a condition associated with installation of one or more of the sterile barrier assembly and the second mounting portion to the first mounting portion. The controller(s) control the illumination device to indicate the condition to a user.

18 Claims, 26 Drawing Sheets

Related U.S. Application Data continuation of application No. 16/703,033, filed on Dec. 4, 2019, now Pat. No. 11,806,096.

(60) Provisional application No. 62/937,529, filed on Nov. 19, 2019, provisional application No. 62/934,771, filed on Nov. 13, 2019, provisional application No. 62/775,126, filed on Dec. 4, 2018.

(51) Int. Cl.
*A61B 90/50* (2016.01)
*A61B 17/00* (2006.01)

(56) References Cited

U.S. PATENT DOCUMENTS

| | | | |
|---|---|---|---|
| 3,021,326 A | 2/1962 | Snider et al. |
| 3,482,567 A | 12/1969 | Franklin |
| 3,483,494 A | 12/1969 | Cromie |
| 3,796,477 A | 3/1974 | Geraci |
| 4,409,738 A | 10/1983 | Renander et al. |
| 4,522,196 A | 6/1985 | Cunningham et al. |
| 4,770,497 A | 9/1988 | Brown |
| 5,042,981 A | 8/1991 | Gross |
| 5,080,108 A | 1/1992 | Roth |
| 5,122,904 A | 6/1992 | Fujiwara et al. |
| 5,184,601 A | 2/1993 | Putman |
| 5,211,501 A | 5/1993 | Nakamura et al. |
| 5,274,500 A | 12/1993 | Dunn |
| 5,413,573 A | 5/1995 | Koivukangas |
| 5,433,221 A | 7/1995 | Adair |
| 5,441,042 A | 8/1995 | Putman |
| 5,457,962 A | 10/1995 | Faries, Jr. et al. |
| 5,467,223 A | 11/1995 | Cleveland, Jr. et al. |
| 5,524,643 A | 6/1996 | Faries, Jr. et al. |
| 5,574,561 A | 11/1996 | Boudreau et al. |
| 5,591,119 A | 1/1997 | Adair |
| 5,626,216 A | 5/1997 | Sperling et al. |
| 5,642,956 A | 7/1997 | Hale |
| 5,669,152 A | 9/1997 | McMurtry |
| 5,762,458 A | 6/1998 | Wang et al. |
| 5,769,554 A | 6/1998 | Slocum |
| 5,785,643 A | 7/1998 | Lynn |
| 5,800,483 A | 9/1998 | Vought |
| 5,816,252 A | 10/1998 | Faries, Jr. et al. |
| 5,853,363 A | 12/1998 | Vought |
| 5,855,583 A | 1/1999 | Wang et al. |
| 5,857,467 A | 1/1999 | Faries, Jr. et al. |
| 5,876,328 A | 3/1999 | Fox et al. |
| 5,891,020 A | 4/1999 | Luber et al. |
| 5,960,794 A | 10/1999 | Shaw |
| 6,050,981 A | 4/2000 | Lampropoulos et al. |
| 6,063,095 A | 5/2000 | Wang et al. |
| 6,065,898 A | 5/2000 | Hale |
| 6,072,569 A | 6/2000 | Bowen |
| 6,102,044 A | 8/2000 | Naidyhorski |
| 6,102,850 A | 8/2000 | Wang et al. |
| 6,116,966 A | 9/2000 | Little et al. |
| 6,132,368 A | 10/2000 | Cooper |
| 6,228,089 B1 | 5/2001 | Wahrburg |
| 6,325,351 B1 | 12/2001 | Hale et al. |
| 6,330,837 B1 | 12/2001 | Charles et al. |
| 6,331,181 B1 | 12/2001 | Tierney et al. |
| 6,346,072 B1 | 2/2002 | Cooper |
| 6,357,445 B1 | 3/2002 | Shaw |
| 6,371,121 B1 | 4/2002 | Faries, Jr. et al. |
| 6,375,610 B2 | 4/2002 | Verschuur |
| 6,398,279 B1 | 6/2002 | Kikut |
| 6,431,530 B1 | 8/2002 | Stamps et al. |
| 6,436,107 B1 | 8/2002 | Wang et al. |
| 6,460,436 B1 | 10/2002 | Salzer et al. |
| 6,460,677 B1 | 10/2002 | Roscoe |
| 6,471,172 B1 | 10/2002 | Lemke et al. |
| 6,491,612 B1 | 12/2002 | Kurup et al. |
| 6,491,701 B2 | 12/2002 | Tierney et al. |

| | | | |
|---|---|---|---|
| 6,533,594 B1 | 3/2003 | Kurup |
| 6,612,310 B2 | 9/2003 | Sklar |
| 6,661,955 B1 | 12/2003 | Calvet et al. |
| 6,699,177 B1 | 3/2004 | Wang et al. |
| 6,720,988 B1 | 4/2004 | Gere et al. |
| 6,729,589 B2 | 5/2004 | Shelef |
| 6,746,172 B2 | 6/2004 | Culpepper |
| 6,755,195 B1 | 6/2004 | Lemke et al. |
| 6,804,547 B2 | 10/2004 | Pelzer et al. |
| 6,805,453 B2 | 10/2004 | Spetzler et al. |
| 6,810,881 B2 | 11/2004 | Faries, Jr. et al. |
| 6,840,895 B2 | 1/2005 | Perry et al. |
| 6,843,252 B2 | 1/2005 | Harrison et al. |
| 6,860,271 B2 | 3/2005 | Faries, Jr. et al. |
| 6,863,071 B2 | 3/2005 | Annett et al. |
| 6,866,671 B2 | 3/2005 | Tierney et al. |
| 6,910,485 B2 | 6/2005 | Faries, Jr. et al. |
| 6,918,395 B2 | 7/2005 | Faries, Jr. et al. |
| 6,945,814 B2 | 9/2005 | Snape et al. |
| 7,002,102 B2 | 2/2006 | Münch et al. |
| 7,027,893 B2 | 4/2006 | Perry et al. |
| 7,048,745 B2 | 5/2006 | Tierney et al. |
| 7,118,582 B1 | 10/2006 | Wang et al. |
| 7,122,032 B2 | 10/2006 | Shinmura et al. |
| 7,137,763 B2 | 11/2006 | Lawson |
| 7,173,779 B2 | 2/2007 | Shelef |
| 7,252,453 B1 | 8/2007 | Little |
| 7,328,086 B2 | 2/2008 | Perry et al. |
| 7,331,967 B2 | 2/2008 | Lee et al. |
| 7,347,210 B2 | 3/2008 | Faries, Jr. et al. |
| 7,350,373 B1 | 4/2008 | Faries, Jr. et al. |
| 7,357,774 B2 | 4/2008 | Cooper |
| 7,418,966 B2 | 9/2008 | Faries, Jr. et al. |
| 7,422,107 B2 | 9/2008 | Burns et al. |
| 7,524,320 B2 | 4/2009 | Tierney et al. |
| 7,559,265 B2 | 7/2009 | Mizuno |
| 7,666,191 B2 | 2/2010 | Orban, III et al. |
| 7,699,855 B2 | 4/2010 | Anderson et al. |
| 7,727,244 B2 | 6/2010 | Orban, III et al. |
| 7,779,716 B2 | 8/2010 | Dellach et al. |
| 7,789,874 B2 | 9/2010 | Yu et al. |
| 7,819,885 B2 | 10/2010 | Cooper |
| 7,850,642 B2 | 12/2010 | Moll et al. |
| 7,886,743 B2 | 2/2011 | Cooper et al. |
| 7,947,050 B2 | 5/2011 | Lee et al. |
| 7,947,051 B2 | 5/2011 | Lee et al. |
| 7,955,322 B2 | 6/2011 | Devengenzo et al. |
| 7,959,860 B2 | 6/2011 | Faries, Jr. et al. |
| 7,963,288 B2 | 6/2011 | Rosenberg et al. |
| 7,963,913 B2 | 6/2011 | Devengenzo et al. |
| 7,972,298 B2 | 7/2011 | Wallace et al. |
| 7,974,681 B2 | 7/2011 | Wallace et al. |
| 8,005,537 B2 | 8/2011 | Hlavka et al. |
| 8,005,570 B2 | 8/2011 | Gloden et al. |
| 8,021,326 B2 | 9/2011 | Moll et al. |
| 8,052,636 B2 | 11/2011 | Moll et al. |
| 8,054,184 B2 | 11/2011 | Cline et al. |
| 8,074,657 B2 | 12/2011 | Scott et al. |
| 8,100,133 B2 * | 1/2012 | Mintz .................. B25J 9/0084 |
| | | 606/1 |
| 8,105,319 B2 | 1/2012 | Doyle et al. |
| 8,105,338 B2 | 1/2012 | Anderson et al. |
| 8,132,816 B2 | 3/2012 | Norton et al. |
| 8,142,447 B2 | 3/2012 | Cooper et al. |
| 8,148,666 B2 | 4/2012 | Faries, Jr. et al. |
| 8,182,469 B2 | 5/2012 | Anderson et al. |
| 8,182,470 B2 | 5/2012 | Devengenzo et al. |
| 8,190,238 B2 | 5/2012 | Moll et al. |
| 8,202,278 B2 | 6/2012 | Orban, III et al. |
| 8,206,053 B2 | 6/2012 | Bennett et al. |
| 8,206,406 B2 | 6/2012 | Orban, III |
| 8,209,840 B2 | 7/2012 | Norton |
| 8,216,250 B2 | 7/2012 | Orban, III et al. |
| 8,220,468 B2 | 7/2012 | Cooper et al. |
| 8,241,208 B2 | 8/2012 | Jiang et al. |
| 8,257,303 B2 | 9/2012 | Moll et al. |
| 8,264,767 B2 | 9/2012 | Nozawa |
| 8,273,076 B2 | 9/2012 | Devengenzo et al. |
| 8,277,505 B1 | 10/2012 | Doty |

(56)               References Cited

U.S. PATENT DOCUMENTS

| | | |
|---|---|---|
| 8,311,626 B2 | 11/2012 | Hlavka et al. |
| 8,333,755 B2 | 12/2012 | Cooper et al. |
| 8,375,808 B2 | 2/2013 | Blumenkranz et al. |
| 8,394,054 B2 | 3/2013 | Wallace et al. |
| 8,409,136 B2 | 4/2013 | Wallace et al. |
| 8,413,948 B2 | 4/2013 | Kemeny |
| 8,460,277 B2 | 6/2013 | Suarez et al. |
| 8,500,132 B2 | 8/2013 | Norton |
| 8,529,582 B2 | 9/2013 | Devengenzo et al. |
| 8,533,930 B2 | 9/2013 | Norton |
| 8,548,779 B2 | 10/2013 | Ortmaier et al. |
| 8,601,667 B2 | 12/2013 | Norton |
| 8,602,031 B2 | 12/2013 | Reis et al. |
| 8,608,773 B2 | 12/2013 | Tierney et al. |
| 8,672,922 B2 | 3/2014 | Loh et al. |
| 8,720,448 B2 | 5/2014 | Reis et al. |
| 8,740,881 B2 | 6/2014 | Ortmaier et al. |
| 8,746,252 B2 | 6/2014 | McGrogan et al. |
| 8,747,288 B2 | 6/2014 | Strotzer et al. |
| 8,784,435 B2 | 7/2014 | Cooper et al. |
| 8,794,993 B2 | 8/2014 | Norton |
| 8,857,821 B2 | 10/2014 | Norton et al. |
| 8,894,634 B2 | 11/2014 | Devengenzo et al. |
| 8,910,637 B2 | 12/2014 | Winer |
| 8,945,095 B2 | 2/2015 | Blumenkranz et al. |
| 8,992,113 B2 | 3/2015 | Campagna et al. |
| 8,998,930 B2 | 4/2015 | Orban, III |
| 9,096,033 B2 | 8/2015 | Holop et al. |
| RE45,681 E | 9/2015 | Perry et al. |
| 9,119,655 B2 | 9/2015 | Bowling et al. |
| 9,194,531 B2 | 11/2015 | Shelef et al. |
| 9,204,933 B2 | 12/2015 | Reis et al. |
| 9,254,572 B2 | 2/2016 | Strotzer |
| 9,259,276 B2 | 2/2016 | Mintz et al. |
| 9,339,342 B2 | 5/2016 | Prisco et al. |
| 9,439,732 B2 | 9/2016 | Devengenzo et al. |
| 9,452,020 B2 | 9/2016 | Griffiths et al. |
| 9,539,060 B2 | 1/2017 | Lightcap et al. |
| 9,622,684 B2 | 4/2017 | Wybo |
| 9,687,312 B2 | 6/2017 | Dachs, II et al. |
| 9,713,509 B2 | 7/2017 | Schuh et al. |
| 9,714,737 B2 | 7/2017 | Nishikawa |
| 9,724,830 B2 | 8/2017 | Norton et al. |
| 9,731,392 B2 | 8/2017 | Takla et al. |
| 9,775,682 B2 | 10/2017 | Quaid et al. |
| 9,981,391 B2 | 5/2018 | Kalb et al. |
| 9,993,313 B2 | 6/2018 | Schuh et al. |
| 10,004,562 B2 | 6/2018 | Kostrzewski et al. |
| 10,016,244 B2 | 7/2018 | Cooper et al. |
| 10,022,193 B2 | 7/2018 | Cooper et al. |
| 10,045,828 B2 | 8/2018 | Dachs, II et al. |
| 10,046,465 B2 | 8/2018 | Goto et al. |
| 10,047,908 B1 | 8/2018 | Bohle et al. |
| 10,052,761 B2 | 8/2018 | Langenfeld |
| 10,076,844 B2 | 9/2018 | Rizk |
| 10,105,855 B2 | 10/2018 | Kalb et al. |
| 10,151,423 B2 | 12/2018 | Shelef et al. |
| 10,231,791 B2 | 3/2019 | Leboeuf, II et al. |
| 10,258,416 B2 | 4/2019 | Mintz et al. |
| 10,265,869 B2 | 4/2019 | Lohmeier et al. |
| 10,271,911 B2 | 4/2019 | Cooper et al. |
| 10,327,849 B2 | 6/2019 | Post |
| 10,335,242 B2 | 7/2019 | Devengenzo et al. |
| 10,342,625 B2 | 7/2019 | Loh et al. |
| 10,342,636 B2 | 7/2019 | Nowatschin et al. |
| 10,357,324 B2 | 7/2019 | Flatt et al. |
| 10,384,356 B2 | 8/2019 | Lohmeier et al. |
| 10,537,400 B2 | 1/2020 | Dachs, II et al. |
| 10,543,051 B2 | 1/2020 | Schena et al. |
| 10,548,673 B2 | 2/2020 | Harris et al. |
| 10,582,980 B2 | 3/2020 | Scheib et al. |
| 10,603,126 B2 | 3/2020 | Karguth et al. |
| 10,624,710 B2 | 4/2020 | Crawford et al. |
| 10,932,837 B2 | 3/2021 | Moctezuma De la Barrera et al. |
| 11,806,096 B2 | 11/2023 | Flatt et al. |

| | | | |
|---|---|---|---|
| 2002/0137358 A1 | 9/2002 | Binnard et al. | |
| 2003/0083673 A1 | 5/2003 | Tierney et al. | |
| 2004/0106894 A1 | 6/2004 | Hunter et al. | |
| 2006/0016061 A1 | 1/2006 | Shelef | |
| 2006/0100610 A1 | 5/2006 | Wallace et al. | |
| 2006/0161138 A1 | 7/2006 | Orban, III et al. | |
| 2006/0191540 A1 | 8/2006 | Lamprich et al. | |
| 2006/0225529 A1 | 10/2006 | Fischer et al. | |
| 2006/0232837 A1 | 10/2006 | Shelef | |
| 2006/0264921 A1 | 11/2006 | Deutsch et al. | |
| 2007/0142824 A1* | 6/2007 | Devengenzo | A61B 34/30 |
| | | | 606/1 |
| 2007/0231063 A1 | 10/2007 | Tsutsumi et al. | |
| 2007/0282311 A1 | 12/2007 | Scott et al. | |
| 2008/0119339 A1 | 5/2008 | Oliver | |
| 2008/0147089 A1 | 6/2008 | Loh et al. | |
| 2008/0182738 A1 | 7/2008 | Grunke et al. | |
| 2008/0218770 A1 | 9/2008 | Moll et al. | |
| 2008/0236598 A1 | 10/2008 | Gobel | |
| 2008/0281301 A1 | 11/2008 | DeBoer et al. | |
| 2009/0088772 A1 | 4/2009 | Blumenkranz | |
| 2009/0248039 A1 | 10/2009 | Cooper et al. | |
| 2009/0306499 A1 | 12/2009 | Van Vorhis et al. | |
| 2010/0009825 A1 | 1/2010 | Norton et al. | |
| 2010/0065068 A1 | 3/2010 | Hamazaki et al. | |
| 2010/0166496 A1 | 7/2010 | Bennett et al. | |
| 2010/0170519 A1 | 7/2010 | Romo et al. | |
| 2010/0241137 A1 | 9/2010 | Doyle et al. | |
| 2010/0268249 A1 | 10/2010 | Stuart | |
| 2010/0268250 A1* | 10/2010 | Stuart | A61B 34/70 |
| | | | 606/130 |
| 2010/0308195 A1 | 12/2010 | Yu et al. | |
| 2011/0015650 A1 | 1/2011 | Choi et al. | |
| 2011/0087238 A1 | 4/2011 | Wang et al. | |
| 2011/0088702 A1 | 4/2011 | King et al. | |
| 2011/0154645 A1 | 6/2011 | Morgan | |
| 2011/0178367 A1 | 7/2011 | Anvari | |
| 2011/0190790 A1 | 8/2011 | Summerer et al. | |
| 2011/0213383 A1 | 9/2011 | Lee et al. | |
| 2011/0238083 A1 | 9/2011 | Moll et al. | |
| 2011/0277775 A1 | 11/2011 | Holop et al. | |
| 2011/0277776 A1 | 11/2011 | McGrogan et al. | |
| 2012/0065472 A1 | 3/2012 | Doyle et al. | |
| 2012/0071752 A1 | 3/2012 | Sewell et al. | |
| 2012/0071821 A1 | 3/2012 | Yu | |
| 2012/0071822 A1 | 3/2012 | Romo et al. | |
| 2012/0071894 A1 | 3/2012 | Tanner et al. | |
| 2012/0071895 A1 | 3/2012 | Stahler et al. | |
| 2012/0080040 A1 | 4/2012 | Skora et al. | |
| 2012/0080041 A1 | 4/2012 | Skora et al. | |
| 2012/0083799 A1 | 4/2012 | Chen et al. | |
| 2012/0083825 A1 | 4/2012 | Stroup et al. | |
| 2012/0116267 A1 | 5/2012 | Kimball et al. | |
| 2012/0191107 A1 | 7/2012 | Tanner et al. | |
| 2012/0209174 A1 | 8/2012 | Moll et al. | |
| 2012/0209291 A1 | 8/2012 | Anderson et al. | |
| 2012/0232566 A1 | 9/2012 | Orban, III et al. | |
| 2012/0239060 A1 | 9/2012 | Orban, III | |
| 2012/0247489 A1 | 10/2012 | Orban, III et al. | |
| 2012/0289974 A1 | 11/2012 | Rogers et al. | |
| 2012/0301067 A1 | 11/2012 | Morgan | |
| 2012/0312308 A1 | 12/2012 | Allen | |
| 2013/0035537 A1 | 2/2013 | Wallace et al. | |
| 2013/0092177 A1 | 4/2013 | Chua et al. | |
| 2013/0174858 A1 | 7/2013 | Annett | |
| 2013/0211401 A1 | 8/2013 | Bailey et al. | |
| 2013/0231679 A1 | 9/2013 | Wallace et al. | |
| 2013/0247921 A1 | 9/2013 | Dye et al. | |
| 2013/0317519 A1 | 11/2013 | Romo et al. | |
| 2013/0331858 A1 | 12/2013 | Devengenzo et al. | |
| 2014/0039681 A1 | 2/2014 | Bowling et al. | |
| 2014/0128885 A1 | 5/2014 | Dachs, II et al. | |
| 2014/0171965 A1 | 6/2014 | Loh et al. | |
| 2014/0326254 A1 | 11/2014 | McGrogan et al. | |
| 2015/0003789 A1 | 1/2015 | Webler et al. | |
| 2015/0047647 A1 | 2/2015 | Winer | |
| 2015/0073437 A1 | 3/2015 | Devengenzo et al. | |
| 2015/0090063 A1* | 4/2015 | Lantermann | B25J 19/0025 |
| | | | 74/490.02 |

(56) References Cited

U.S. PATENT DOCUMENTS

| | | |
|---|---|---|
| 2015/0133960 A1 | 5/2015 | Lohmeier et al. |
| 2015/0142012 A1 | 5/2015 | Lohmeier et al. |
| 2015/0148817 A1 | 5/2015 | Lohmeier et al. |
| 2015/0148818 A1 | 5/2015 | Lohmeier et al. |
| 2015/0150638 A1 | 6/2015 | Lohmeier et al. |
| 2015/0173841 A1 | 6/2015 | Orban |
| 2015/0202009 A1 | 7/2015 | Nussbaumer et al. |
| 2015/0305815 A1 | 10/2015 | Holop et al. |
| 2016/0039059 A1 | 2/2016 | Takla et al. |
| 2016/0052146 A1 | 2/2016 | Berrocal et al. |
| 2016/0059424 A1 | 3/2016 | Zachary et al. |
| 2016/0184036 A1 | 6/2016 | Solomon et al. |
| 2016/0184037 A1 | 6/2016 | Cooper et al. |
| 2016/0220320 A1 | 8/2016 | Crawford et al. |
| 2016/0242861 A1 | 8/2016 | Flatt et al. |
| 2016/0256225 A1 | 9/2016 | Crawford et al. |
| 2016/0256231 A1* | 9/2016 | Ogawa .................... G05G 1/02 |
| 2016/0278875 A1 | 9/2016 | Crawford et al. |
| 2016/0338783 A1 | 11/2016 | Romo et al. |
| 2016/0361124 A1 | 12/2016 | Dachs, II et al. |
| 2016/0361131 A1 | 12/2016 | Dachs, II et al. |
| 2016/0374766 A1 | 12/2016 | Schuh |
| 2017/0007334 A1 | 1/2017 | Crawford et al. |
| 2017/0020630 A1 | 1/2017 | Johnson et al. |
| 2017/0065357 A1 | 3/2017 | Schuh |
| 2017/0079727 A1 | 3/2017 | Crawford et al. |
| 2017/0119339 A1 | 5/2017 | Johnson et al. |
| 2017/0144230 A1 | 5/2017 | Rosso et al. |
| 2017/0165006 A1 | 6/2017 | Woods et al. |
| 2017/0165012 A1 | 6/2017 | Chaplin et al. |
| 2017/0172669 A1 | 6/2017 | Berkowitz et al. |
| 2017/0172671 A1 | 6/2017 | Miller et al. |
| 2017/0172674 A1 | 6/2017 | Hanuschik et al. |
| 2017/0181801 A1 | 6/2017 | Griffiths et al. |
| 2017/0265774 A1 | 9/2017 | Johnson et al. |
| 2017/0333136 A1 | 11/2017 | Hladio et al. |
| 2017/0348063 A1 | 12/2017 | Braun et al. |
| 2017/0354468 A1 | 12/2017 | Johnson et al. |
| 2017/0367782 A1 | 12/2017 | Schuh et al. |
| 2018/0000472 A1 | 1/2018 | Beira |
| 2018/0049819 A1 | 2/2018 | Harris et al. |
| 2018/0110572 A1 | 4/2018 | Flatt |
| 2018/0110576 A1 | 4/2018 | Kopp |
| 2018/0126546 A1 | 5/2018 | Vaders |
| 2018/0132839 A1 | 5/2018 | Friedrich et al. |
| 2018/0147018 A1 | 5/2018 | Crawford et al. |
| 2018/0168752 A1 | 6/2018 | Scheib et al. |
| 2018/0168753 A1 | 6/2018 | Scheib et al. |
| 2018/0168761 A1 | 6/2018 | Vargas et al. |
| 2018/0168762 A1 | 6/2018 | Scheib et al. |
| 2018/0168763 A1 | 6/2018 | Scheib et al. |
| 2018/0206931 A1 | 7/2018 | Scheib |
| 2018/0214221 A1 | 8/2018 | Crawford et al. |
| 2018/0221098 A1 | 8/2018 | Forsyth et al. |
| 2018/0256259 A1 | 9/2018 | Crawford |
| 2018/0271604 A1 | 9/2018 | Grout et al. |
| 2018/0271616 A1 | 9/2018 | Schuh et al. |
| 2018/0279993 A1 | 10/2018 | Crawford et al. |
| 2018/0280097 A1 | 10/2018 | Cooper et al. |
| 2018/0296283 A1 | 10/2018 | Crawford et al. |
| 2018/0304475 A1 | 10/2018 | Zachary et al. |
| 2018/0310808 A1 | 11/2018 | Laser et al. |
| 2018/0310997 A1 | 11/2018 | Peine et al. |
| 2018/0311001 A1 | 11/2018 | Prisco |
| 2018/0316139 A1 | 11/2018 | Berrocal et al. |
| 2018/0325610 A1 | 11/2018 | Cameron et al. |
| 2018/0333213 A1 | 11/2018 | Johnson et al. |
| 2018/0360546 A1 | 12/2018 | Blumenkranz et al. |
| 2019/0000561 A1 | 1/2019 | Decker et al. |
| 2019/0000569 A1 | 1/2019 | Crawford et al. |
| 2019/0000580 A1 | 1/2019 | Scheib et al. |
| 2019/0009416 A1 | 1/2019 | Kalb et al. |
| 2019/0029765 A1 | 1/2019 | Crawford et al. |
| 2019/0099232 A1 | 4/2019 | Soto et al. |
| 2019/0142540 A1 | 5/2019 | Chow |
| 2019/0150901 A1 | 5/2019 | Ponzer et al. |
| 2019/0167365 A1 | 6/2019 | Chaplin et al. |
| 2019/0183594 A1 | 6/2019 | Shelton, IV et al. |
| 2019/0192240 A1 | 6/2019 | Mintz et al. |
| 2019/0216554 A1 | 7/2019 | Kapadia |
| 2019/0223966 A1 | 7/2019 | Holop et al. |
| 2019/0223976 A1 | 7/2019 | Krinninger et al. |
| 2019/0231448 A1 | 8/2019 | McBrien et al. |
| 2019/0231455 A1 | 8/2019 | Cooper et al. |
| 2019/0231464 A1 | 8/2019 | Wixey et al. |
| 2019/0254763 A1 | 8/2019 | Lambrecht et al. |
| 2019/0274766 A1 | 9/2019 | Holop et al. |
| 2019/0274780 A1 | 9/2019 | Nowatschin et al. |
| 2019/0282313 A1 | 9/2019 | Devengenzo et al. |
| 2019/0282315 A1 | 9/2019 | Loh et al. |
| 2019/0290379 A1 | 9/2019 | Flatt et al. |
| 2019/0298461 A1 | 10/2019 | Holop et al. |
| 2019/0298470 A1 | 10/2019 | Ramstad et al. |
| 2019/0298471 A1 | 10/2019 | Holop |
| 2019/0328473 A1 | 10/2019 | Chassot et al. |
| 2020/0046394 A1 | 2/2020 | Cau |
| 2020/0058284 A1 | 2/2020 | Miller et al. |
| 2020/0061847 A1 | 2/2020 | Dixon |
| 2020/0069385 A1 | 3/2020 | Ago et al. |
| 2020/0170724 A1 | 6/2020 | Flatt et al. |
| 2020/0253678 A1 | 8/2020 | Hulford et al. |
| 2022/0249176 A1 | 8/2022 | Malackowski et al. |
| 2024/0008940 A1 | 1/2024 | Flatt et al. |

FOREIGN PATENT DOCUMENTS

| | | | |
|---|---|---|---|
| GB | 2447239 A | 9/2008 | |
| GB | 2483154 A | 2/2012 | |
| JP | H03256686 A | 11/1991 | |
| JP | 2006297499 A | 11/2006 | |
| WO | WO-0033755 A1 * | 6/2000 | ............. G16H 40/63 |
| WO | 2007005555 A2 | 1/2007 | |
| WO | 2009092701 A1 | 7/2009 | |
| WO | 2009123891 A1 | 10/2009 | |
| WO | 2009123925 A1 | 10/2009 | |
| WO | 2010121107 A1 | 10/2010 | |
| WO | 2010121117 A1 | 10/2010 | |
| WO | 2011037394 A2 | 3/2011 | |
| WO | 2013075204 A1 | 5/2013 | |
| WO | 2013075205 A1 | 5/2013 | |
| WO | 2013159932 A1 | 10/2013 | |
| WO | 2014162217 A1 | 10/2014 | |
| WO | 2014165828 A1 | 10/2014 | |
| WO | 2015023834 A1 | 2/2015 | |
| WO | 2015052629 A1 | 4/2015 | |
| WO | 2015110542 A1 | 7/2015 | |
| WO | 2015142814 A1 | 9/2015 | |
| WO | 2015142815 A1 | 9/2015 | |
| WO | 2016028388 A1 | 2/2016 | |
| WO | 2016134266 A1 | 8/2016 | |
| WO | 2018111575 A1 | 6/2018 | |
| WO | 2018189729 A1 | 10/2018 | |
| WO | 2019023378 A1 | 1/2019 | |
| WO | 2019023383 A2 | 1/2019 | |
| WO | 2019023386 A2 | 1/2019 | |
| WO | 2019023390 A2 | 1/2019 | |
| WO | 2019023393 A1 | 1/2019 | |
| WO | 2019054880 A1 | 3/2019 | |

OTHER PUBLICATIONS

Culpepper, Martin L et al., "Design of Low-Cost Kinematic Couplings Using Formed Balls and Grooves in Sheet Metal Parts" Massachusetts Institute of Technology, Cambridge, MA, Oct. 2003, 4 pages.

English language abstract and machine-assisted English translation for DE 10 2012 008 535 extracted from espacenet.com database on Sep. 30, 2019, 36 pages.

English language abstract and machine-assisted English translation for JP 2006-297499 A extracted from espacenet. com database on Sep. 29, 2023, 10 pages.

(56)                    References Cited

OTHER PUBLICATIONS

English language abstract and machine-assisted English translation for JPH 03-256686 A extracted from espacenet. com database on Apr. 1, 2024, 7 pages.

English language abstract for WO 2011/037394 extracted from espacenet.com database on Apr. 20, 2020, 1 page.

English language abstract for WO 2013/159932 extracted from espacenet. com database on Apr. 20, 2020, 2 pages.

English language abstract for WO2009092701 extracted from espacenet. com database on Apr. 20, 2020, 2 pages.

Furse, J.E., "Kinematic Design of Fine Mechanisms in Instruments", J. Phys. E. Sci. Instrum., vol. 14, 1981, 8 pages.

Hale, Layton C. et al., "Optimal Design Technique for Kinematic Coupling", Precision Engineering, Journal of the International Societies for Precision Engineering and Nanotechnology, vol. 25, 2001, pp. 114-127.

International Search Report for Application No. PCT/US2016/018691 dated Jun. 1, 2016, 2 pages.

International Search Report for Application No. PCT/US2019/064429 dated Jul. 7, 2020, 9 pages.

Invitation to Pay Additional Fees/Partial International Search Report for Application No. PCT/US 2019/064429 dated Mar. 6, 2020, 3 pages.

Slocum, Alexander H., "Design of Three-Groove Kinematic Couplings" Department of Mechanical Engineering, Massachusetts Institute of Technology, Cambridge, MA, 1992, 10 pages.

* cited by examiner

ROBOTIC SURGICAL SYSTEM WITH ILLUMINATION DEVICE TO INDICATE MOUNTING ASSEMBLY INSTALLATION CONDITION

RELATED APPLICATIONS

This application is a continuation of U.S. patent application Ser. No. 18/372,721, filed Sep. 26, 2023, which is a continuation of U.S. patent application Ser. No. 16/703,033, filed Dec. 4, 20219, now U.S. Pat. No. 11,806,096, which claims priority to and the benefit of U.S. Provisional Patent App. No. 62/775,126, filed on Dec. 4, 2018, U.S. Provisional Patent App. No. 62/934,771, filed on Nov. 13, 2019, and U.S. Provisional Patent App. No. 62/937,529, filed on Nov. 19, 2019, the entire contents of each of the above applications being hereby incorporated by reference.

TECHNICAL FIELD

The present disclosure relates, generally, to mounting systems for surgical components and, more specifically, to a mounting system with a sterile barrier assembly for use in coupling surgical components.

BACKGROUND

Sterile barrier assemblies such as surgical drapes are known for establishing barriers between surgical components during surgery. For instance, a surgical drape may be used to provide a barrier between a robotic arm and an end effector attached to the robotic arm. In surgery, the robotic arm is treated as being nonsterile, while the end effector is sterile. The surgical drape creates a barrier between the robotic arm and the end effector to prevent contamination of a sterile field in which the end effector is operating.

Typically, surgical drapes placed between the robotic arm and the end effector have perforations or other openings through which different connections can be made between the robotic arm and the end effector, such as mechanical connections and/or electrical connections. Such perforations are acceptable, so long as they are covered during the surgery. If the end effector fails during the surgery and needs to be replaced, or if a different end effector is desired, and the perforations become uncovered, standard operating room sterility protocol may dictate that the surgical drape requires replacement before a different end effector can be installed. Removal of the surgical drape and installation of a new surgical drape takes up valuable time, so replacement is undesirable.

Other surgical drapes are not intentionally perforated, but instead are compressed between the robotic arm and the end effector. When compressed, if the surgical drape is formed of thin plastic, unintended rips or tears may occur. Even when the surgical drape does remain intact, positioning of the end effector on the robotic arm is imprecise as a result of the compressibility of the surgical drape. For example, the surgical drape may compress unequally. Further, a thick drape made out of conventional draping materials could deflect under normal end effector loads. Small deflections are magnified out to a tool center point (TCP) of the end effector and can become intolerable due to errors in positioning accuracy of the TCP.

Therefore, there is a need in the art for addressing one or more of these deficiencies.

SUMMARY

A mounting system is provided for coupling first and second surgical components. The mounting system comprise a first mounting portion associated with the first surgical component and a second mounting portion associated with the second surgical component. The second mounting portion comprises a tensioner movable between a first position and a second position. The mounting system further comprises a sterile barrier assembly. The sterile barrier assembly comprises a coupling configured to releasably secure to the first mounting portion and to releasably receive the second mounting portion when the tensioner of the second mounting portion is in the first position. A plurality of kinematic couplers are configured to engage the mounting portions and are arranged to provide a kinematic coupling between the mounting portions through the sterile barrier assembly to constrain six degrees of freedom of movement between the surgical components when the tensioner of the second mounting portion is in the second position.

An end effector is provided for releasably attaching to a first mounting portion of a surgical robot through a sterile barrier assembly having a coupling and a plurality of kinematic couplers. The end effector comprises a housing for supporting an energy applicator and a second mounting portion attached to the housing. The second mounting portion comprises a tensioner movable between a first position and a second position. The second mounting portion is configured to be releasably coupled to the coupling of the sterile barrier assembly when the tensioner of the second mounting portion is in the first position. The second mounting portion comprises a plurality of contact surfaces for engaging the plurality of kinematic couplers of the sterile barrier assembly.

A sterile barrier assembly is provided for releasably attaching to a first mounting portion of a first surgical component and to a second mounting portion of a second surgical component having a tensioner. The sterile barrier assembly comprises an interface configured to receive a drape and a coupling operatively attached to the interface and configured to releasably secure to the first mounting portion and to releasably receive the second mounting portion when the tensioner of the second mounting portion is in a first position. A plurality of kinematic couplers are supported by the interface and are configured to engage the mounting portions. The plurality of kinematic couplers are arranged to provide a kinematic coupling between the mounting portions to constrain six degrees of freedom of movement between the surgical components when the tensioner of the second mounting portion is in a second position.

A surgical robot is provided for releasably receiving a second mounting portion of an end effector through a sterile barrier assembly having a coupling and a plurality of kinematic couplers. The second mounting portion has a tensioner movable from a first position to a second position. The surgical robot comprises a robotic arm having a first mounting portion configured to releasably receive the second mounting portion of the end effector through the sterile barrier assembly. The first mounting portion comprises a plurality of contact surfaces for engaging the plurality of kinematic couplers of the sterile barrier assembly. The first mounting portion further comprises a loading mechanism configured to apply a preload force to the second mounting portion through the sterile barrier assembly upon movement of the tensioner from the first position to the second position.

A surgical system is provided which comprises: a second mounting portion associated with a surgical component; a sterile barrier assembly; a surgical robot comprising a robotic arm having a first mounting portion configured to releasably receive the sterile barrier assembly and the first mounting portion through the sterile barrier assembly; an illumination device coupled to the robotic arm; and one or more controllers coupled to one or more sensors and being configured to: detect, using measurements from the one or more sensors, a condition associated with installation of one or more of the sterile barrier assembly and the second mounting portion to the first mounting portion; and control the illumination device to indicate the condition to a user.

A method of operating a surgical system is provided, with the surgical system comprising a second mounting portion associated with a surgical component, a sterile barrier assembly, a surgical robot comprising a robotic arm having a first mounting portion configured to releasably receive the sterile barrier assembly and the first mounting portion through the sterile barrier assembly, an illumination device coupled to the robotic arm, and one or more controllers coupled to one or more sensors, the method comprising the one or more controllers: detecting, using measurements from the one or more sensors, a condition associated with installation of one or more of the sterile barrier assembly and the second mounting portion to the first mounting portion; and controlling the illumination device to indicate the condition to a user.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
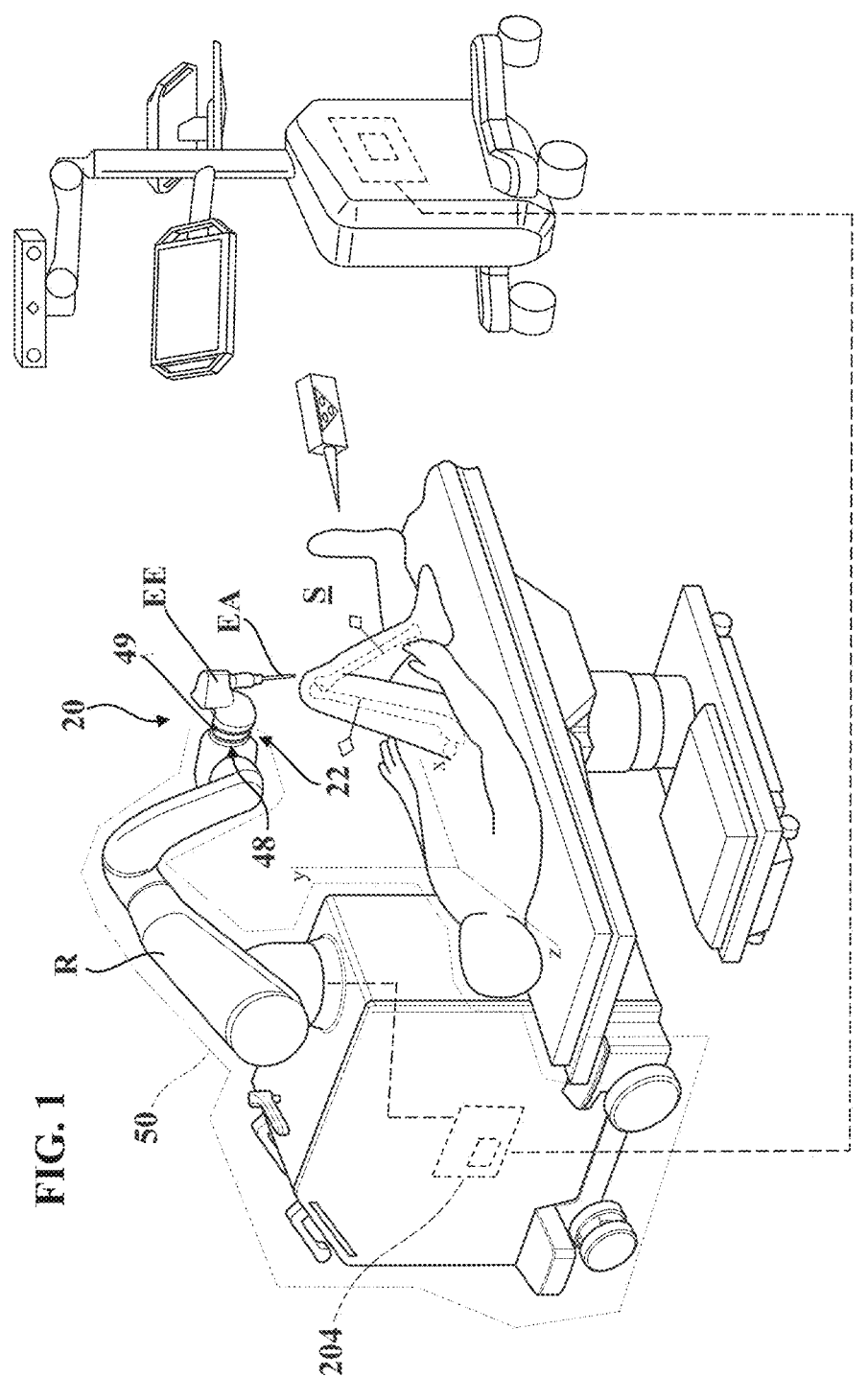
FIG. 1 is a perspective view of a robotic surgical system including a mounting system interposed between a robotic arm and an end effector.
Figures 2, 3:
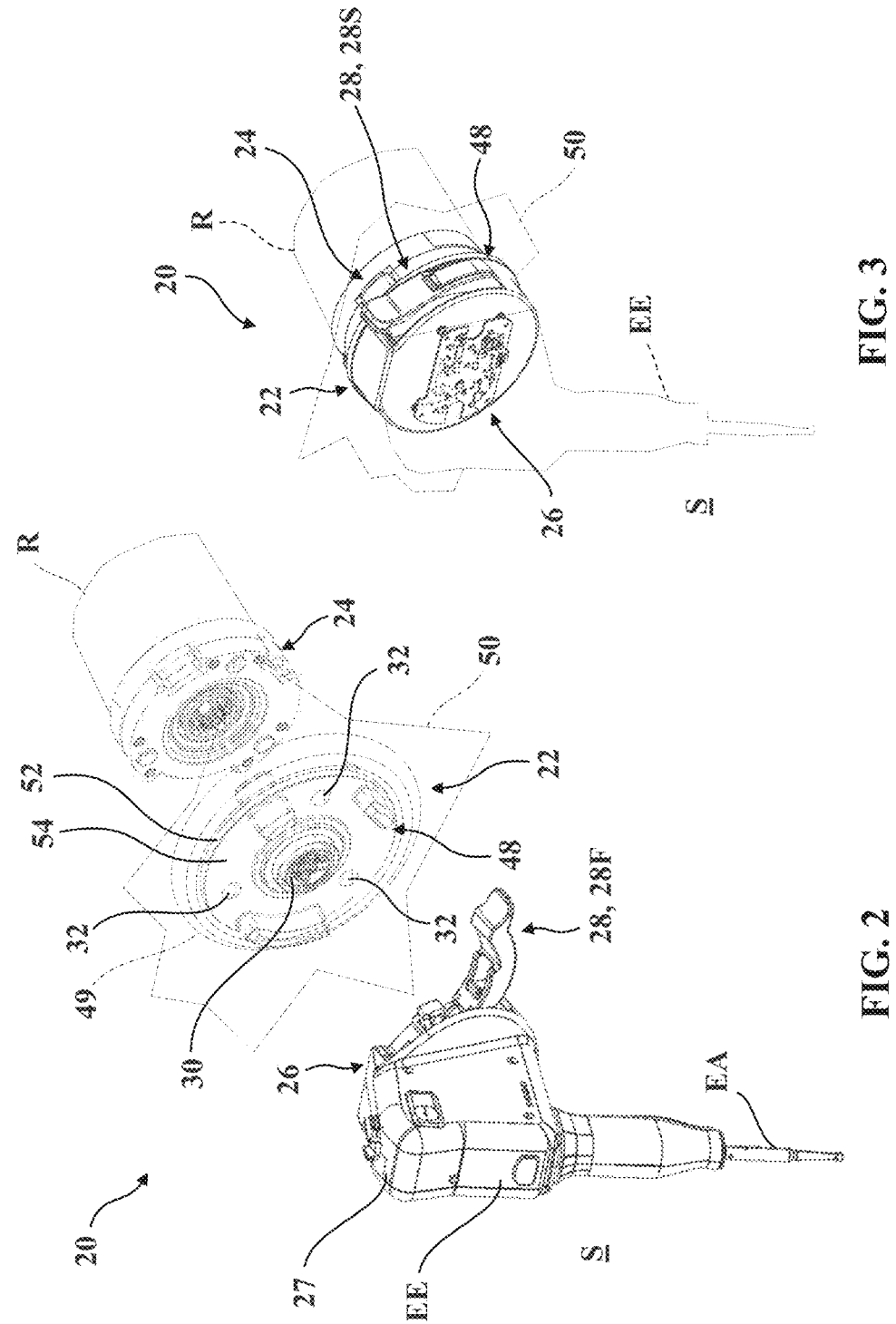
FIG. 2 is a partially exploded perspective view of the mounting system shown with a first mounting portion attached to the robotic arm, a second mounting portion attached to the end effector, and a sterile barrier assembly to interconnect the mounting portions.
FIG. 3 is a perspective view of the mounting system of FIG. 1 shown with first and second mounting portions and the sterile barrier assembly arranged in a loaded configuration.

Referring now to FIGS. 1-3, a mounting system 20 is shown for kinematically coupling first and second surgical components using a sterile barrier assembly 22. In the representative examples described herein, the first surgical component is a surgical robot having a robotic arm R and the second surgical component is an end effector EE for attaching to the robotic arm R. The robotic arm R and the end effector EE may be like those described in U.S. Patent Application Publication No. 2018/0110572, filed Oct. 20, 2017, entitled "Systems and Tools for use with Surgical Robotic Manipulators," the entire disclosure of which is hereby incorporated herein by reference. It should be appreciated that the mounting system 20 can be employed to kinematically couple any surgical components using the sterile barrier assembly 22.

Referring to FIGS. 2 and 3, the robotic arm R includes a first mounting portion 24 and the end effector EE includes a second mounting portion 26. The sterile barrier assembly 22 is located between the first and second mounting portions 24, 26 to establish a barrier between the robotic arm R and the end effector EE during surgery. This barrier separates the robotic arm R from a sterile field S in which the end effector EE operates. During surgery, the robotic arm R is considered nonsterile and the barrier reduces the potential for migration of contaminants from the robotic arm R into the sterile field S.

In order to facilitate releasable attachment of the sterile barrier assembly 22 and the end effector EE to the robotic arm R, the second mounting portion 26 is provided with a tensioner 28 which is movable between a first position 28F and a second position 28S, as described in greater detail below, and the sterile barrier assembly 22 is provided with a coupling 30 and a plurality of kinematic couplers 32.

The coupling 30 is configured to releasably secure to the first mounting portion 24 and to releasably receive the second mounting portion 26 when the tensioner 28 of the second mounting portion 26 is in the first position 28F. The kinematic couplers 32 are configured to engage the mounting portions 24, 26 and are arranged to provide a kinematic coupling between the mounting portions 24, 26 through the sterile barrier assembly 22 to constrain six degrees of freedom of movement between the surgical components when the tensioner 28 of the second mounting portion 26 is in the second position 28S.

As noted above, the mounting portions 24, 26 are configured to be releasably and kinematically coupled together with the sterile barrier assembly 22. Kinematic coupling provides a rigid connection between the mounting portions 24, 26 so that positioning between the mounting portions 24, 26 can be deterministic and repeatable. As a result of this rigid, deterministic, and repeatable connection, errors in positioning the end effector EE that may otherwise be associated with a more flexible connection between an end effector and a robotic arm can be reduced. Kinematic coupling exactly constrains the number of degrees of freedom that are to be constrained, i.e., no degree of freedom is over constrained. For instance, in the representative example illustrated herein there are six degrees of freedom between the mounting portions 24, 26 (three translational and three rotational). Thus, kinematic coupling constrains exactly those six degrees of freedom with respect to the end effector EE.

In certain examples, different end effectors EE can be used for different purposes. For example, a plurality of end effectors, each with a different energy applicator EA (e.g., bur, drill, reamer, saw, ultrasonic tip, impactor, etc.) can be used with the same robotic arm R to carry out various functions during a surgical procedure, e.g., burring, drilling, reaming, sawing, ablating, impacting, etc., with all of the end effectors EE having the same second mounting portion 26 to releasably attach to the first mounting portion 24 as described herein. In the version shown, the second mounting portion 26 is attached to or otherwise integrated into housings 27 of the end effectors EE. The energy applicator EA is supported by and carried by the housing 27 to perform its function during the surgical procedure.

Figure 4:
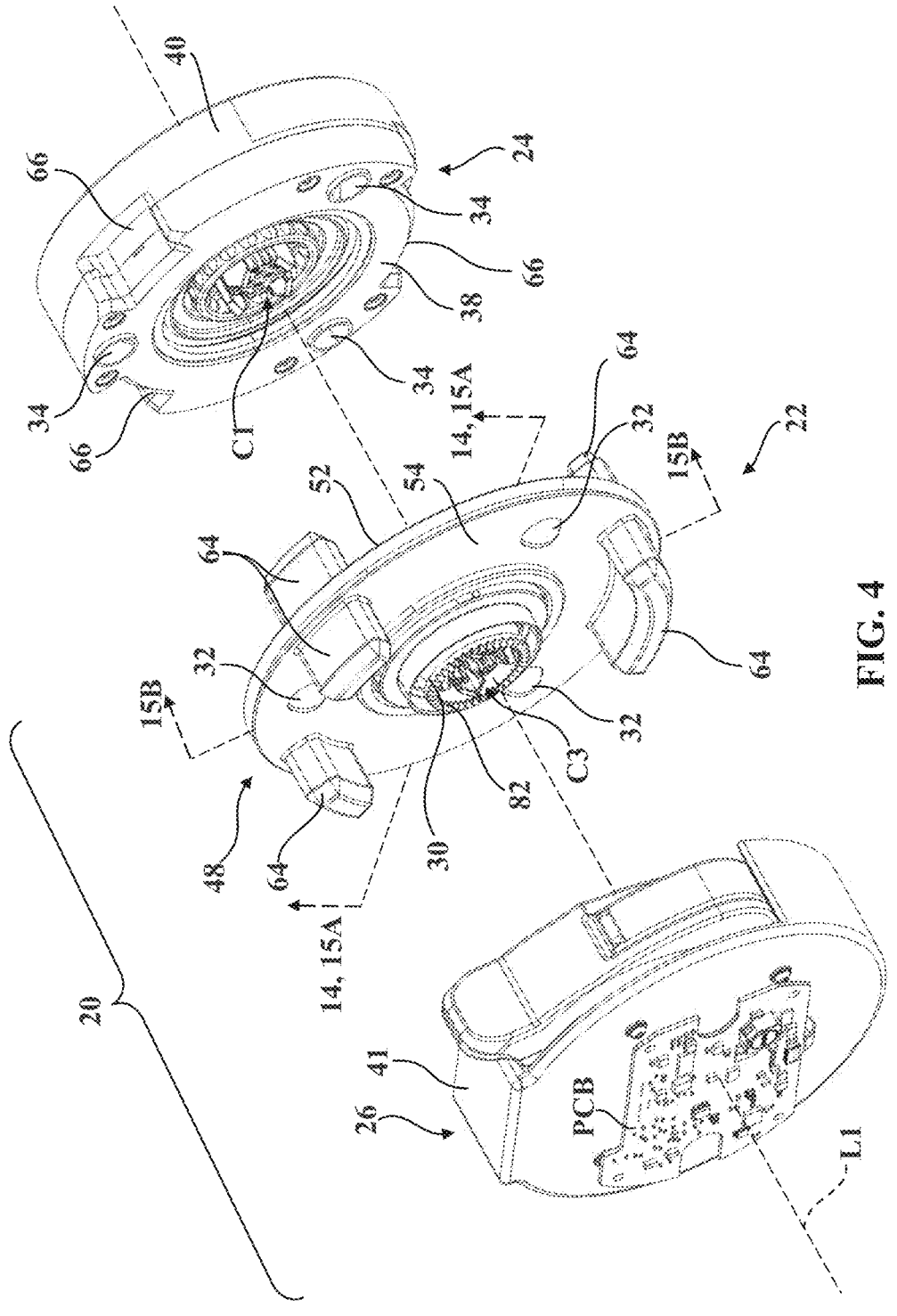
FIG. 4 is a partially exploded perspective view of the mounting system of FIG. 3 shown with the first mounting portion, the second mounting portion, and the sterile barrier assembly arranged spaced from each other.
Figures 5, 5A:
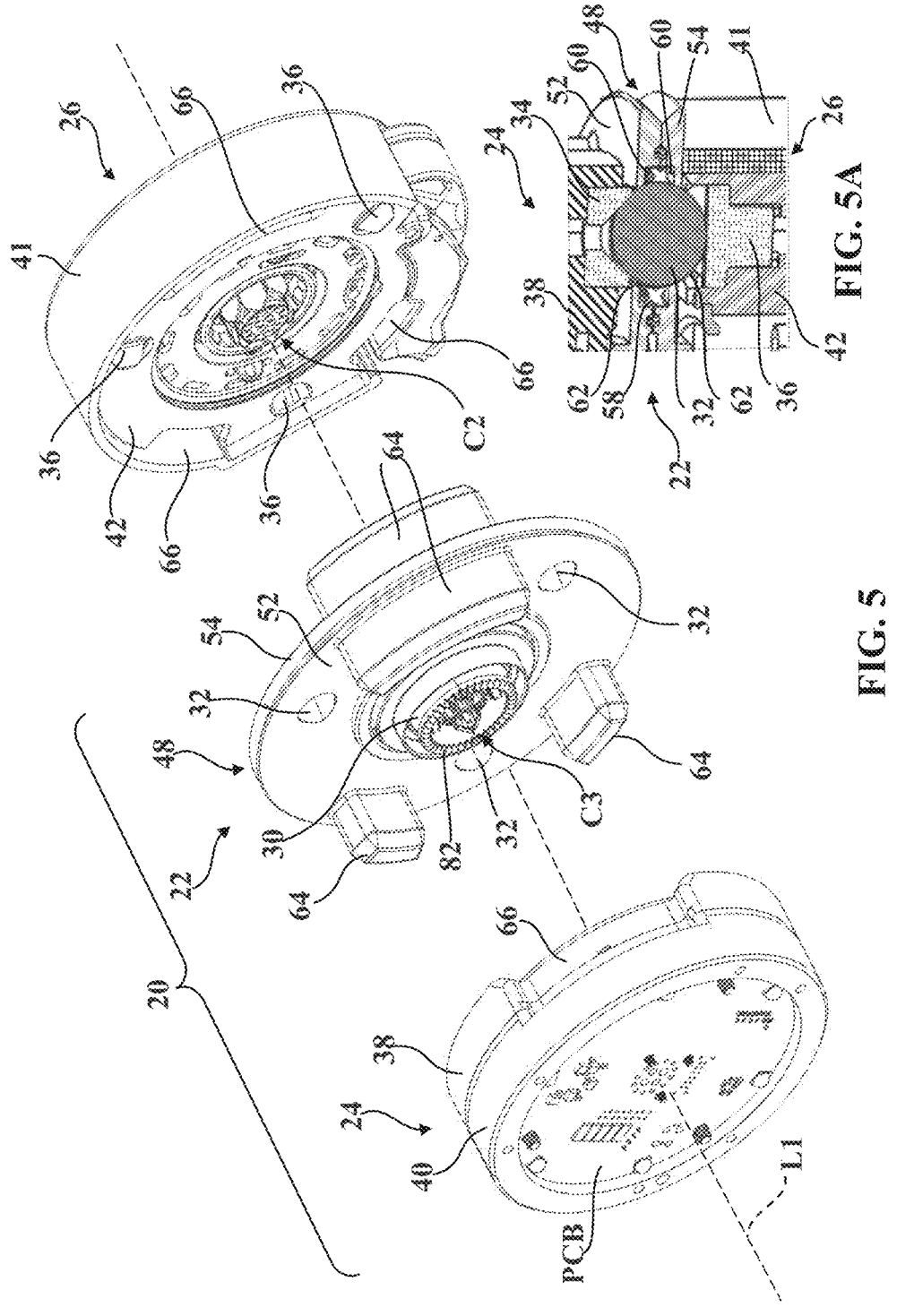
FIG. 5 is another partially exploded perspective view of the mounting system of FIG. 3.
FIG. 5A is a partial perspective section view illustrating a kinematic coupler contained within an interface of the sterile barrier assembly.

Referring to FIGS. 4 and 5, the sterile barrier assembly 22 employs the plurality of kinematic couplers 32 to kinematically couple the mounting portions 24, 26. In the representative example illustrated herein, the kinematic couplers 32 are realized as three spherical balls configured to constrain the six degrees of freedom of movement between the surgical components. In one example, the balls have polished, corrosion-resistant surfaces, so that under certain loads submicron repeatability in positioning the mounting portions 24, 26 can be achieved. The balls may be formed of ceramic, stainless steel, or other suitable materials. By way of non-limiting example, the balls may be formed of silicon carbide or tungsten carbide. The balls may be precision machined to very tight tolerances, for example less than fifty millionths of an inch. During use, the balls are seated in first and second pluralities of receptacles 34, 36 of the respective first and second mounting portions 24, 26. The receptacles 34, 36 are sized and shaped to receive the balls 32.

In the example shown, the first mounting portion 24 includes a first mounting plate 38 and a hub mount 40 fixed to the first mounting plate 38. The hub mount 40 is adapted for attachment to the robotic arm R, such as via one or more fasteners or bolts (not shown). Here, the first plurality of receptacles 34 are operatively attached to the first mounting plate 38 (e.g., fixed to the first mounting plate 38 via fasteners, welding, press-fit, or the like). The second mounting portion 26 similarly includes a second mounting plate 42 (see FIG. 5) with a cover 41 which is adapted for attachment to the end effector EE, such as via one or more fasteners or bolts (not shown). Here, the second plurality of receptacles 36 are operatively attached to the second mounting plate 42 (e.g., fixed to the second mounting plate 42 via fasteners, welding, press-fit, or the like). The first mounting portion 24 includes a first plurality of contact surfaces, defined by the first plurality of receptacles 34, for engaging the plurality of kinematic couplers 32. Similarly, the second mounting portion 26 includes a second plurality of contact surfaces, defined by the second plurality of receptacles 36, for engaging the plurality of kinematic couplers 32. The contact surfaces are shaped to cooperate with the kinematic couplers 32 to constrain the six degrees of freedom of movement between the end effector EE and the robotic arm R. In one version, the second plurality of contact surfaces are configured to provide only six contact points with the plurality of kinematic couplers 32.

The first plurality of receptacles 34 of the first mounting portion 24 each have a contact surface with a conical configuration (also referred to as a cone receptacle). The second plurality of receptacles 36 of the second mounting portion 26 each have a contact surface with a generally V-shaped groove (also referred to as a V-grooved receptacle). More specifically, the contact surfaces of these V-grooved receptacles 36 are in the shape of a gothic arch. The contact surfaces act as constraint surfaces for the kinematic coupling described above. It will be appreciated that different types, arrangements, and configurations of receptacles 34, 36 could be employed to effect kinematic coupling between the mounting portions 24, 26. By way of non-limiting example, flat or planar receptacles could be utilized for certain applications.

While the representative example illustrated herein depicts the first mounting portion 24 with three cone receptacles and the second mounting portion 26 with three V-grooved receptacles, it will be appreciated that each mounting portion 24, 26 could utilize different types of receptacles 34, 36 arranged in different ways. By way of non-limiting example, the first mounting portion 24 could conceivably employ two V-grooved receptacles and one cone receptacle. The first mounting portion 24 could also employ three V-grooved receptacles. Similarly, it will be appreciated that the second mounting portion 26 could employ receptacles configured in any way sufficient to constrain exactly six degrees of freedom with respect to the kinematic couplers 32. By way of non-limiting example, the second mounting portion 26 could employ one cone receptacle to constrain three degrees of freedom, one V-grooved receptacle to constrain two degrees of freedom, and one flat receptacle to constrain one degree of freedom, for a total of six degrees of freedom constrained.

The receptacles 34, 36 may be formed of steel or other suitably rigid materials and may be formed as separate components rigidly connected to the mounting portions 24, 26 or may be integral with the mounting portions 24, 26 in which case the receptacles 34, 36 simply comprise constraint surfaces integral with the mounting portions 24, 26 for securing the balls. The receptacles 34, 36 may be attached to the mounting portions 24, 26 in numerous ways via numerous structures, arrangements, or configurations. When the mounting portions 24, 26 are brought together in approximate final orientation with the sterile barrier assembly 22 positioned therebetween, as shown in FIG. 3, the kinematic couplers 32 of the sterile barrier assembly 22, e.g., the balls, self-seat into the receptacles 34, 36. The kinematic couplers 32, receptacles 34, 36, and their arrangement may be like those described in U.S. Patent Application Publication No. 2016/0242861, filed on Feb. 19, 2016, entitled "Sterile Barrier Assembly, Mounting System, and Method for Coupling Surgical Components," which is hereby incorporated herein by reference in its entirety.

In the representative example illustrated herein, the sterile barrier assembly 22 comprises an interface 48 and a drape 50 operatively attached to the interface 48. The drape 50, shown in FIGS. 1-3, may be secured between first and second interface plates 52, 54 of the interface 48, which are secured to each other with fasteners so as to retain the drape 50 therebetween, or the drape 50 may be attached to one of the interface plates 52, 54, e.g., on a side or an outer surface thereof. Additionally, or alternatively, the drape 50 may be attached to a separate component that is releasably attached to the interface 48 prior to the surgical procedure, such as a ring assembly 49 (see FIG. 2). One example of the ring assembly 49 is shown and described in U.S. patent application Ser. No. 16/151,439, entitled "Sterile Drape Assembly for Surgical Robot," filed on Oct. 4, 2018, which is hereby incorporated herein by reference in its entirety. It will be appreciated that the interface plates 52, 54 could be operatively attached to each other in any suitable way, such as by welding.

The drape 50 has an interior surface and an exterior surface. The interior surface is placed adjacent to the robotic arm R during surgery. In the example shown in FIG. 1, the drape 50 is fitted to the robotic arm R to generally encompass the robotic arm R. The drape 50 is formed of at least one of polyethylene, polyurethane, and polycarbonate. The drape 50 may be attached to the interface 48 by ultrasonic welding, tape, adhesive, or the like, or the drape 50 may be attached to the ring assembly 49, which is releasably coupled to the interface 48. The drape 50 is attached to the interface 48 so that no perforations are present, i.e., the drape forms a continuous barrier with the interface 48. The drape 50 is absent in several of the Figures to better illustrate other components.

The kinematic couplers 32 are contained between the interface plates 52, 54. To this end, referring to FIG. 5A, which shows the mounting portions 24, 26 secured together through the sterile barrier assembly 22, the sterile barrier assembly 22 is provided with seals 58 associated with each of the kinematic couplers 32 (one shown in FIG. 5A). Each of the interface plates 52, 54 is provided with pockets 60 and ball apertures 62 arranged adjacent to the pockets 60 and defined through the interface plates 52, 54. The kinematic couplers 32 protrude through the ball apertures 62 which, in turn, cooperate with the seals 58 to retain the kinematic couplers 32 between the interface plates 52, 54. The kinematic couplers 32 are located so that the barrier remains unbroken between the interface plates 52, 54, the seals 58, and the kinematic couplers 32 to reduce the potential for migration of contaminants through the interface 48. Thus, the drape 50 and the interface 48 provide a continuous barrier to the migration of contaminants from the robotic arm R into the sterile field S.

As is best illustrated in FIGS. 4 and 5, in one example, the sterile barrier assembly 22 comprises one or more indexing fingers 64, and at least one of the mounting portions 24, 26 defines one or more indexing recesses 66 shaped to receive the indexing fingers 64 to align the kinematic couplers 32 with respect to at least one of the mounting portions 24, 26, and associated receptacles 34, 36. In the representative example illustrated herein, the sterile barrier assembly 22 is provided with a total of six indexing fingers 64, three of which are associated with indexing recesses 66 formed in the second mounting plate 42 of the second mounting portion 26, and three of which are associated with indexing recesses 66 formed in the first mounting plate 38 of the first mounting portion 24.

It will be appreciated that the indexing fingers 64 and/or indexing recesses 66 could have any suitable shape, arrangement, or configuration sufficient to promote proper orientation of the sterile barrier assembly 22 and the mounting portions 24, 26. For example, indexing fingers 64 could be present on the mounting portions 24, 26, with corresponding indexing recesses 66 formed in the sterile barrier assembly 22. In the version illustrated, one of the indexing fingers 64 has a different size and/or shape than the other indexing fingers 64 and the indexing recesses 66 in the mounting portions 24, 26 are correspondingly sized/shaped such that the sterile barrier assembly 22 can only be aligned in one orientation relative to the mounting portions 24, 26.

Still referring to FIGS. 4 and 5, alignment and orientation of the sterile barrier assembly 22 and the mounting portions 24, 26 prior to or concurrent with attachment therebetween may advantageously be implemented to promote corresponding alignment of one or more communication interfaces employed to facilitate communication between the end effector EE and the robotic arm R. Here, the first mounting portion 24, the second mounting portion 26, and the sterile barrier assembly 22, could each employ one or more connectors, such as sealed electrical connectors, adapted to provide electrical connection between the first mounting portion 24 and the second mounting portion 26 to facilitate communication between the robotic arm R and the end effector EE during use. In the version shown, first, second, and third connectors C1, C2, C3 are employed. Different types of communication through the connectors C1, C2, C3 are contemplated without limitation, including electrical, pneumatic, optical, hydraulic, and the like, which may comprise, represent, or consist of signals, power, data, and/or other types of information communicated between the robotic arm R and the end effector EE. It will be appreciated that the use of sealed connectors, such as may be integrated in the coupling 30 of the sterile barrier assembly 22, and the mounting portions 24, 26 ensures that contaminants do not enter the sterile field S when the end effector EE is removed from the sterile barrier assembly 22.

Figures 5B, 5C, 5D:
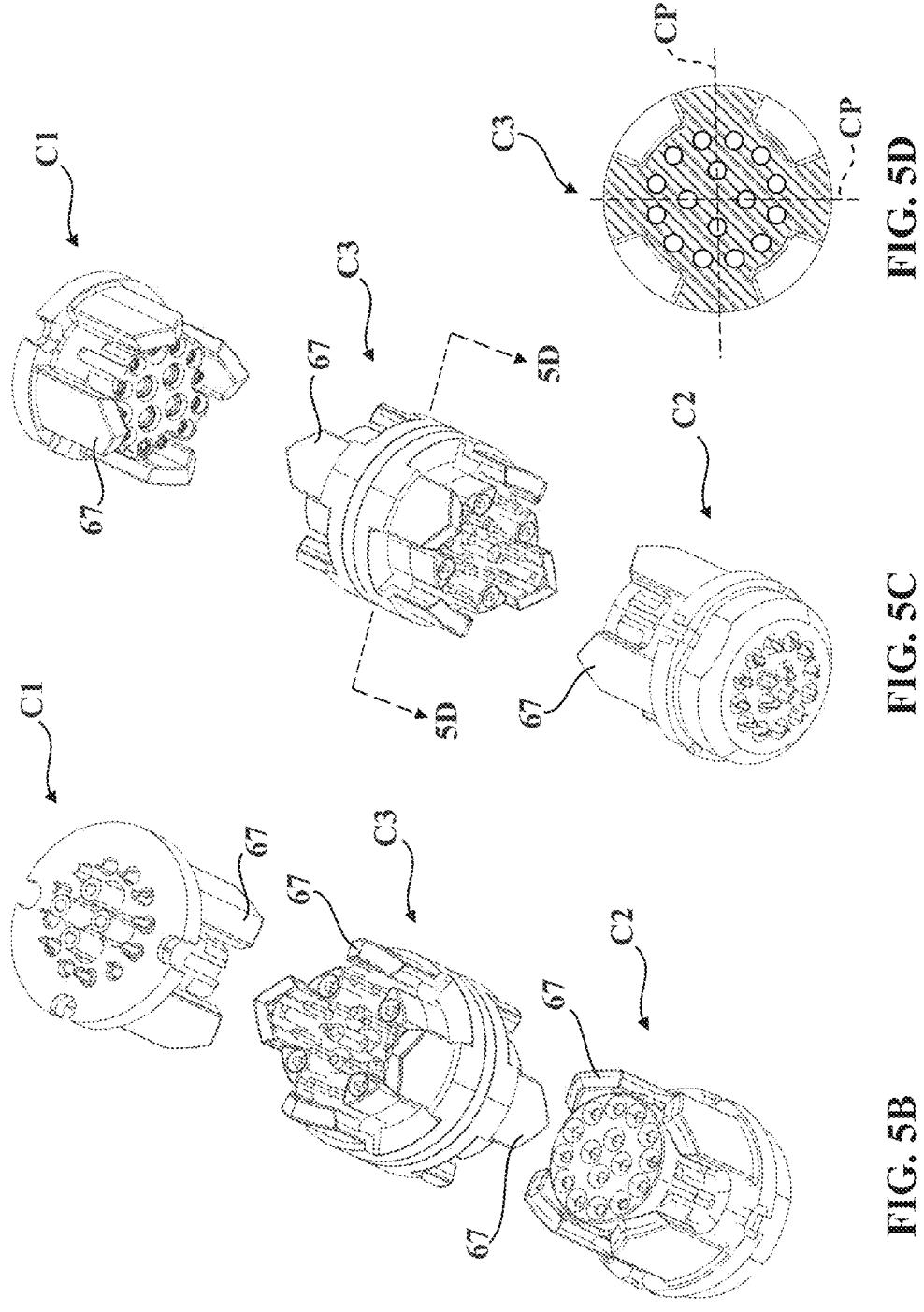
FIGS. 5B and 5C are exploded perspective views of connectors.
FIG. 5D is a section view of one of the connectors taken generally along the line 5D-5D in FIG. 5C.

In the version illustrated, the third connector C3 is carried by the sterile barrier assembly 22 and is rotatably supported within the coupling 30 to rotate relative to the interface 48 about a longitudinal axis L1 defined through the mounting portions 24, 26, and the sterile barrier assembly 22. One or both of the first and second connectors C1, C2 are fixed from rotation, or at least partially restricted from rotation, in their corresponding mounting portions 24, 26. Referring to FIGS. 5B and 5C, owing to the rotatable nature of the third connector C3, the connectors C1, C2, C3 may have mating, castellated projections 67 to self-align at least the third connector C3 with the first connector C1 when attaching the sterile barrier assembly 22 to the first mounting portion 24. In other words, since the third connector C3 is free to rotate in the coupling 30, when the sterile barrier assembly 22 is attached to the first mounting portion 24, the projections 67 appropriately clock the third connector C3 in one of a plurality of discrete positions, e.g., one of four discrete positions, relative to the first connector C1. To this end, as shown in FIG. 5D, the third connector C3 may have a symmetric arrangement of pins with respect to central planes CP through the third connector C3.

During use, referring briefly back to FIGS. 2 and 3, the first mounting portion 24 may be a generally permanent fixture of the robotic arm R. As medical personnel begin preparations for a surgical procedure, the sterile barrier assembly 22 is first attached to the first mounting portion 24 and the robotic arm R is covered with the drape 50 of the sterile barrier assembly 22. The mounting system 20 is configured to facilitate releasable attachment of the sterile barrier assembly 22 to the first mounting portion 24, as well as releasable attachment of the second mounting portion 26 to the sterile barrier assembly 22, in order to ensure a repeatable and deterministic kinematic coupling of the end effector EE (and/or other end effectors EE during the procedure) without disrupting the sterile field S encompassing the robotic arm R as afforded by the sterile barrier assembly 22. Additionally, a preload force is applied to secure the second mounting portion 26 to the first mounting portion 24, through the sterile barrier assembly 22 by virtue of rotating the tensioner 28 from the first position 28F (FIG. 2) to the second position 28S (FIG. 3). FIGS. 6 through 13 are exploded views of the first mounting portion 24, the sterile barrier assembly 22, and the second mounting portion 26, with some components omitted for clarity. The components of the first mounting portion 24, the sterile barrier assembly 22, and the second mounting portion 26 that facilitate coupling and loading of the sterile barrier assembly 22 onto the first mounting portion 24, and the second mounting portion 26 onto the sterile barrier assembly 22 are described below.

Figure 14A:
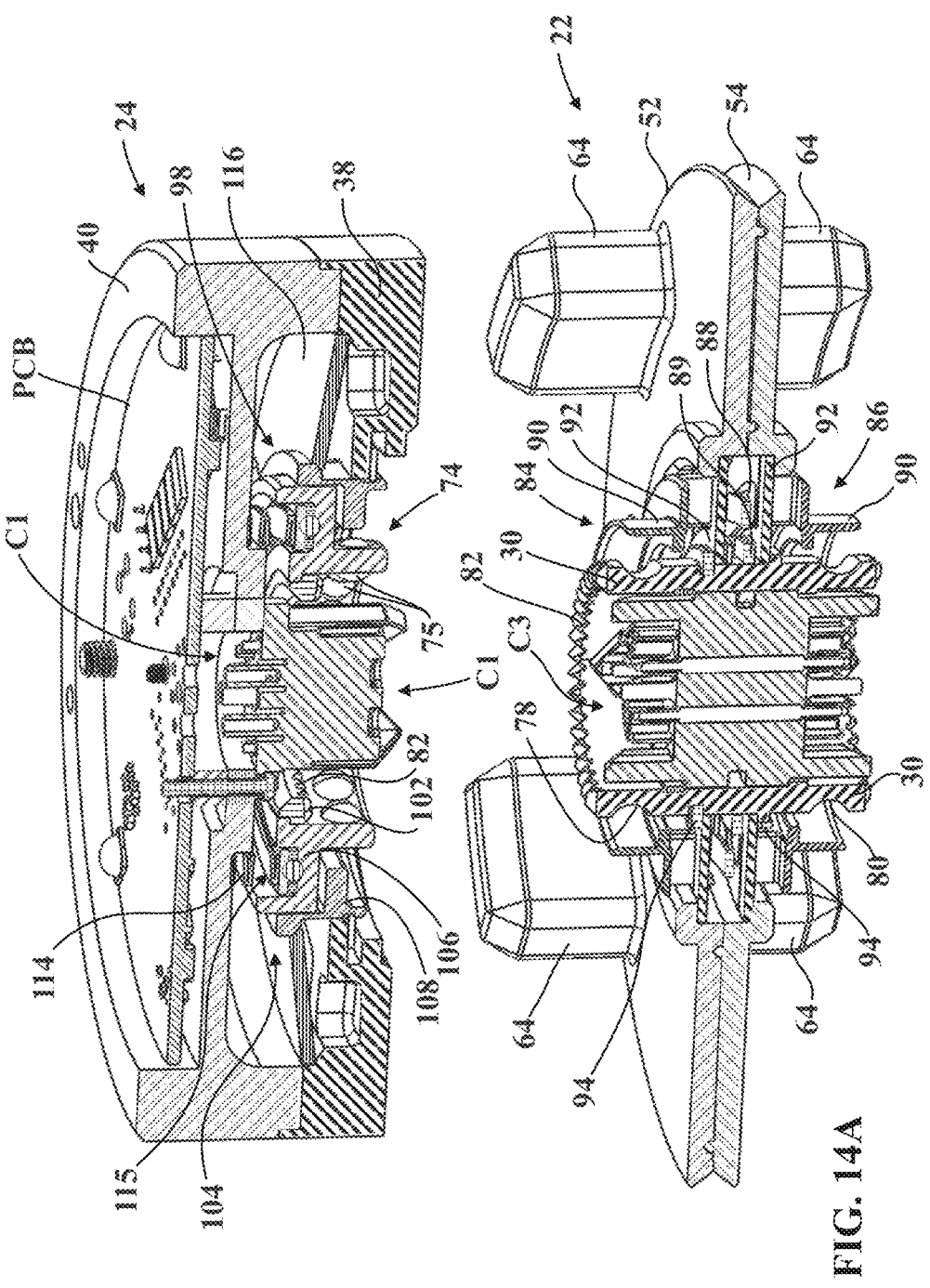
FIGS. 14A-14C are perspective section views taken generally along line 14-14 in FIG. 4 illustrating connection of the sterile barrier assembly onto the first mounting portion.
Figure 14B:
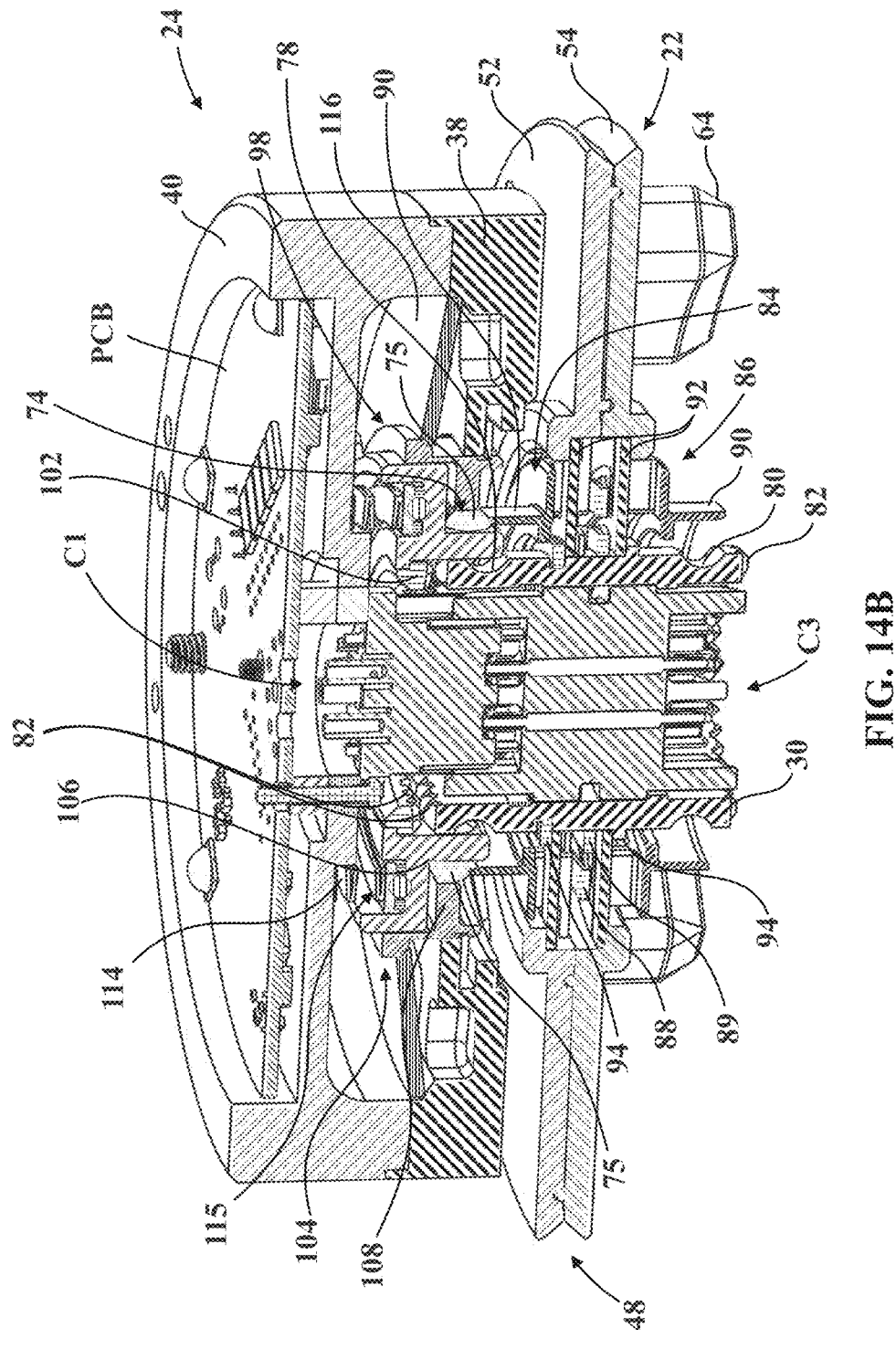
Figure 14C:
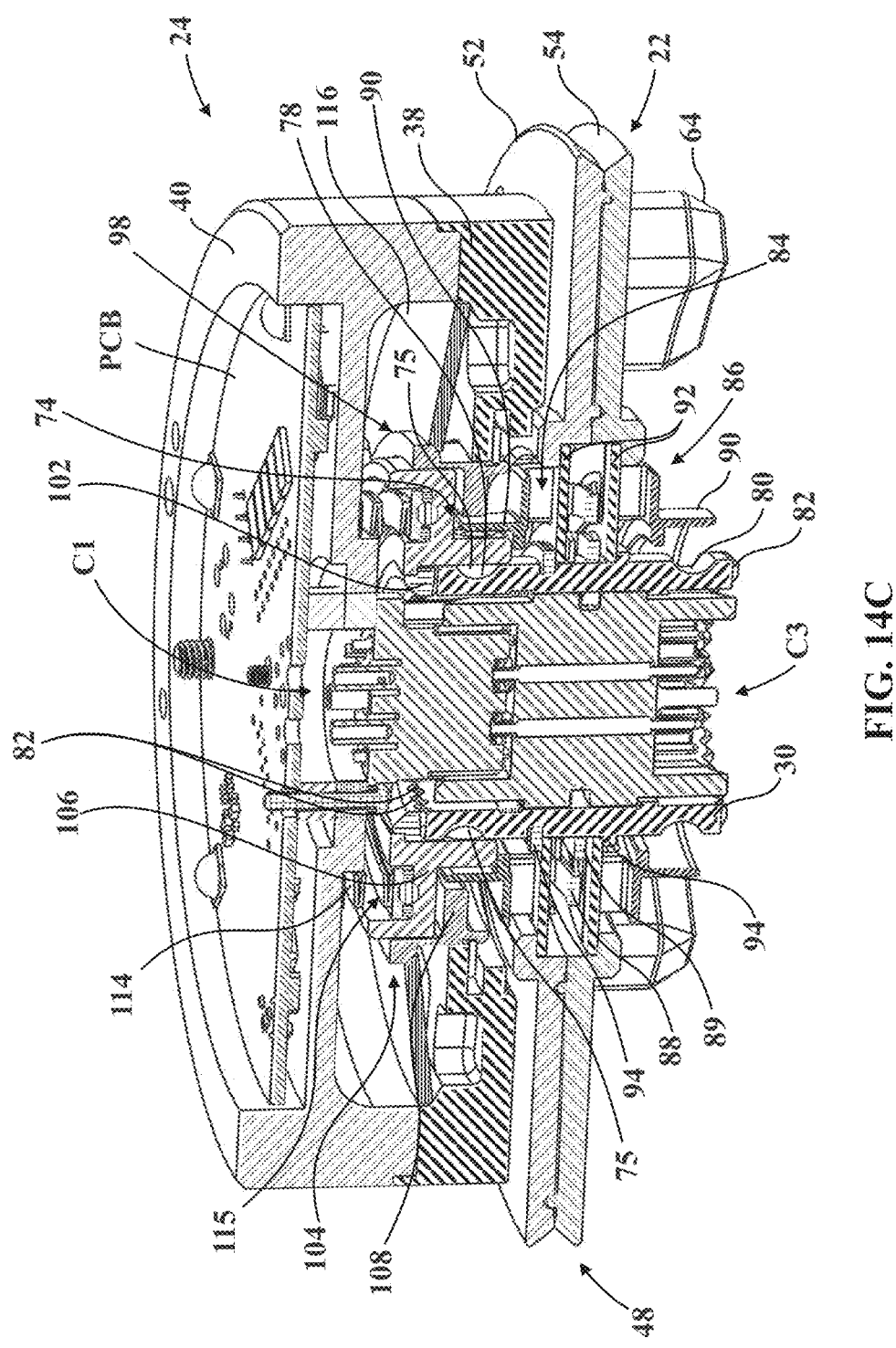
Figure 15A:
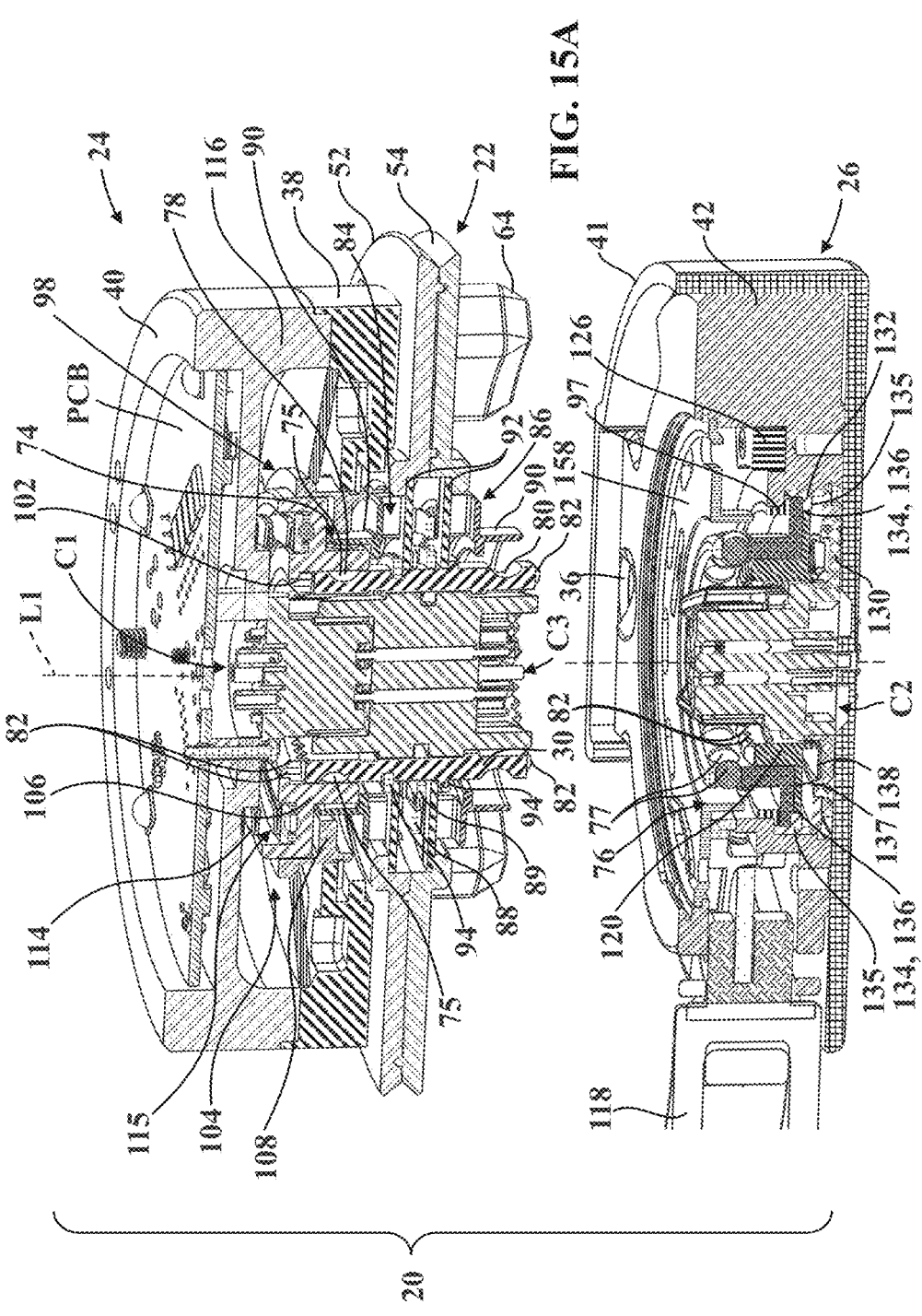
FIG. 15A is a perspective section view taken generally along line 15A-15A in FIG. 4 illustrating the second mounting portion, the first mounting portion, and the sterile barrier assembly, which is shown connected to the first mounting portion.
Figure 15B:
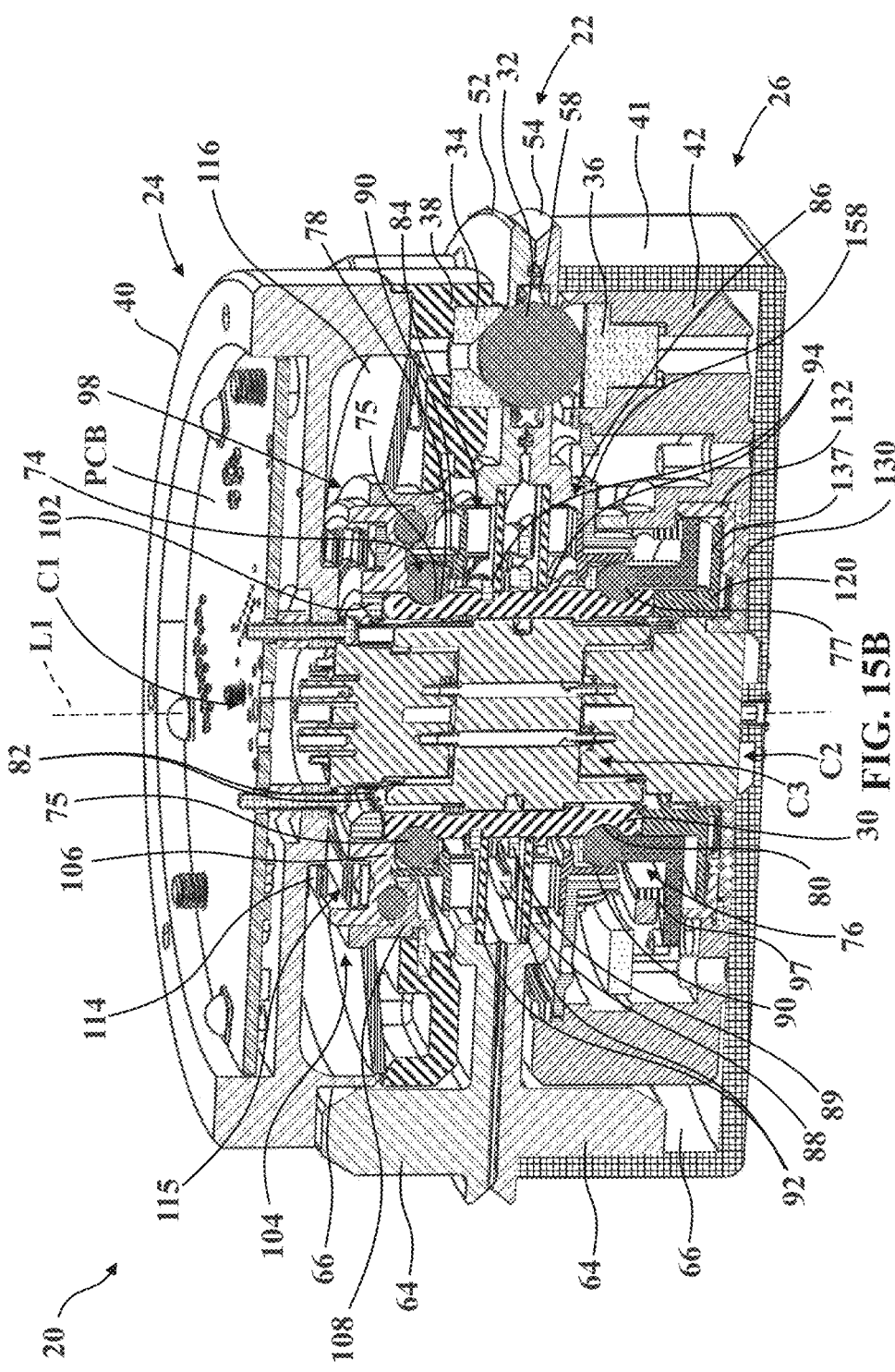
FIG. 15B is another perspective section view taken generally along line 15B-15B in FIG. 4 to illustrate connection of the second mounting portion to the sterile barrier assembly.

Referring to FIGS. 14A-15B, first and second lock assemblies are provided to releasably lock the sterile barrier assembly 22 to the first mounting portion 24 (see progression from FIG. 14A to FIG. 14C) and, subsequently, to releasably lock the second mounting portion 26 to the sterile barrier assembly 22 (see the progression from FIG. 15A to FIG. 15B). The lock assemblies help facilitate the releasable connection between the sterile barrier assembly 22 and the mounting portions 24, 26 in absence of the kinematic coupling afforded when the tensioner 28 is moved to the second position 28S. This configuration contributes to ease of use in that the sterile barrier assembly 22 can be secured to the first mounting portion 24, and the second mounting portion 26 can be secured to the sterile barrier assembly 22, in advance of movement of the tensioner 28 to the second position 28S to apply the preload force, which may be desirable for certain applications, such as where the end effector EE is relatively heavy or awkward for a single person to handle.

Figure 6:
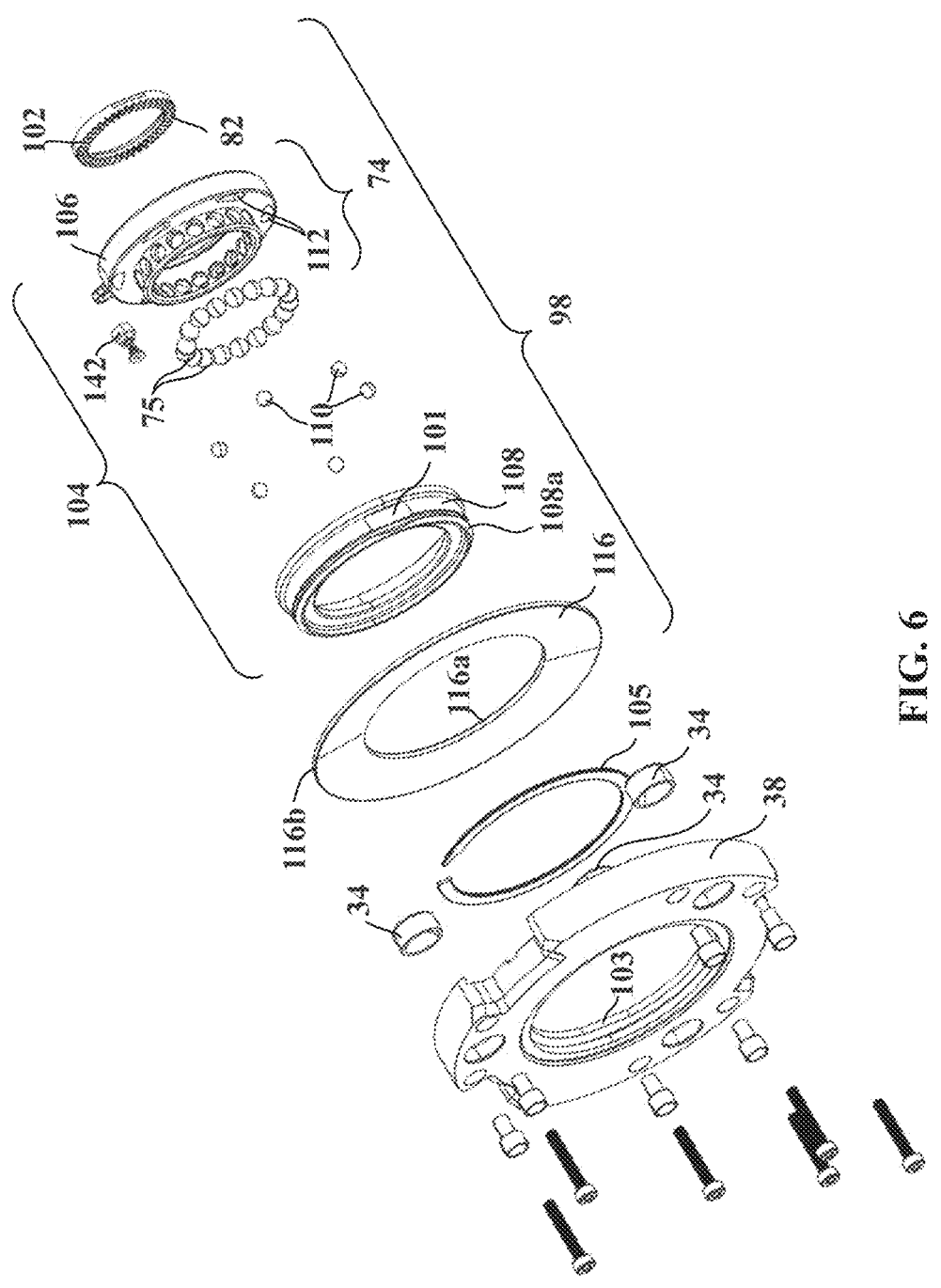
FIG. 6 is an exploded perspective view of a first set of components of the first mounting portion of FIG. 4.
Figure 7:
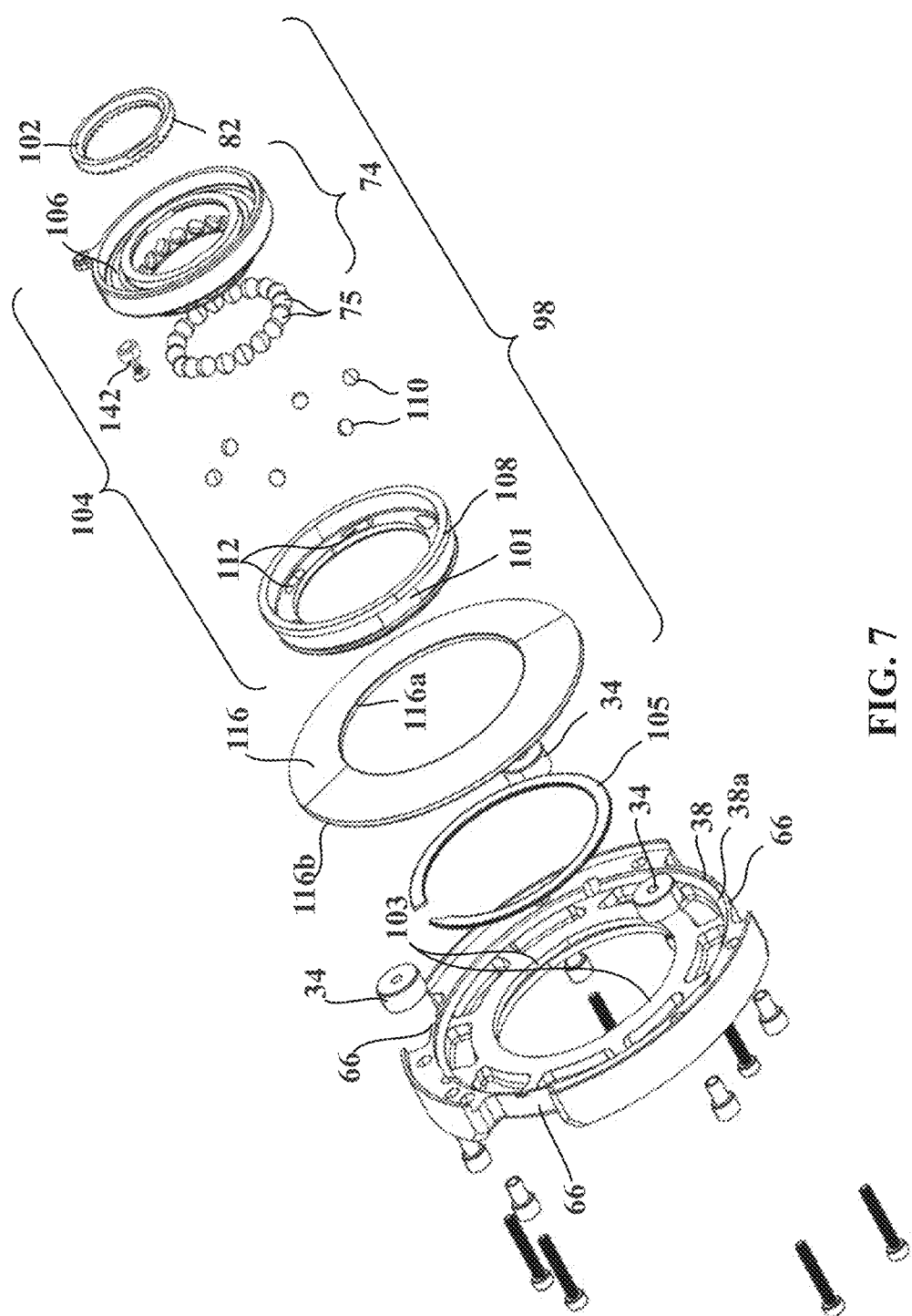
FIG. 7 is another exploded perspective view of the first set of components of the first mounting portion of FIG. 4.
Figure 8:
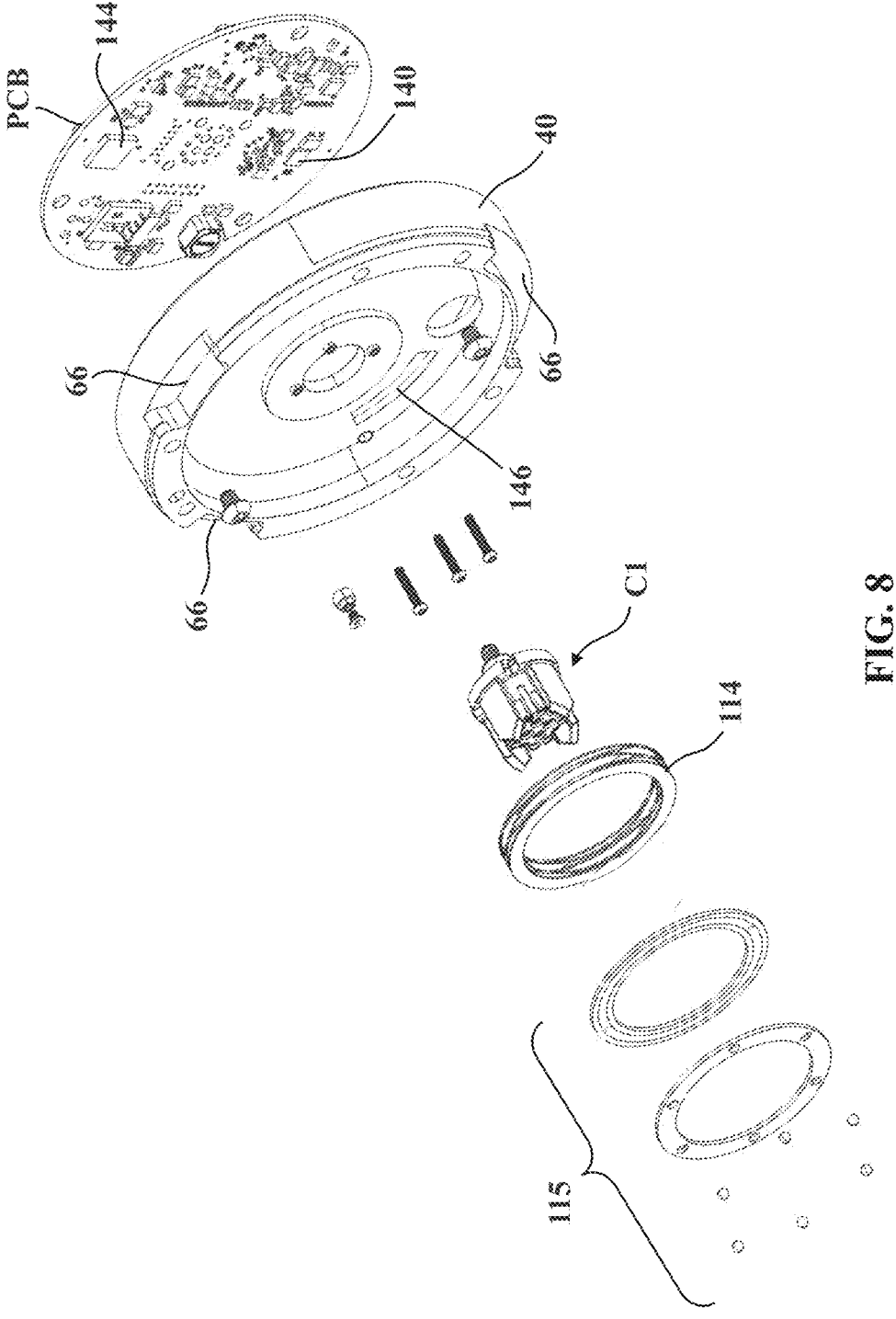
FIG. 8 is an exploded perspective view of a second set of components of the first mounting portion of FIG. 4.
Figure 9:
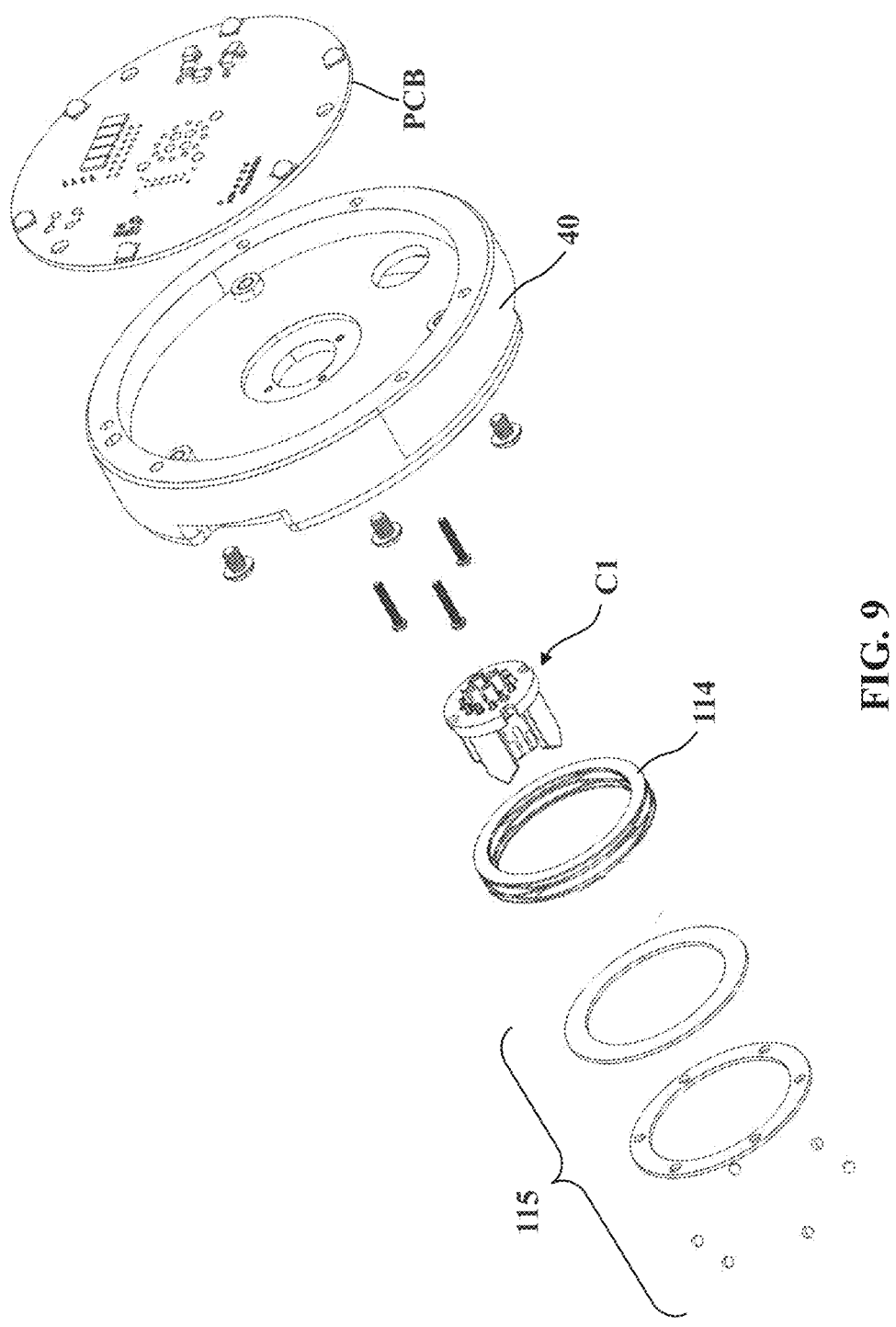
FIG. 9 is another exploded perspective view of the second set of components of the first mounting portion of FIG. 4.
Figure 11:
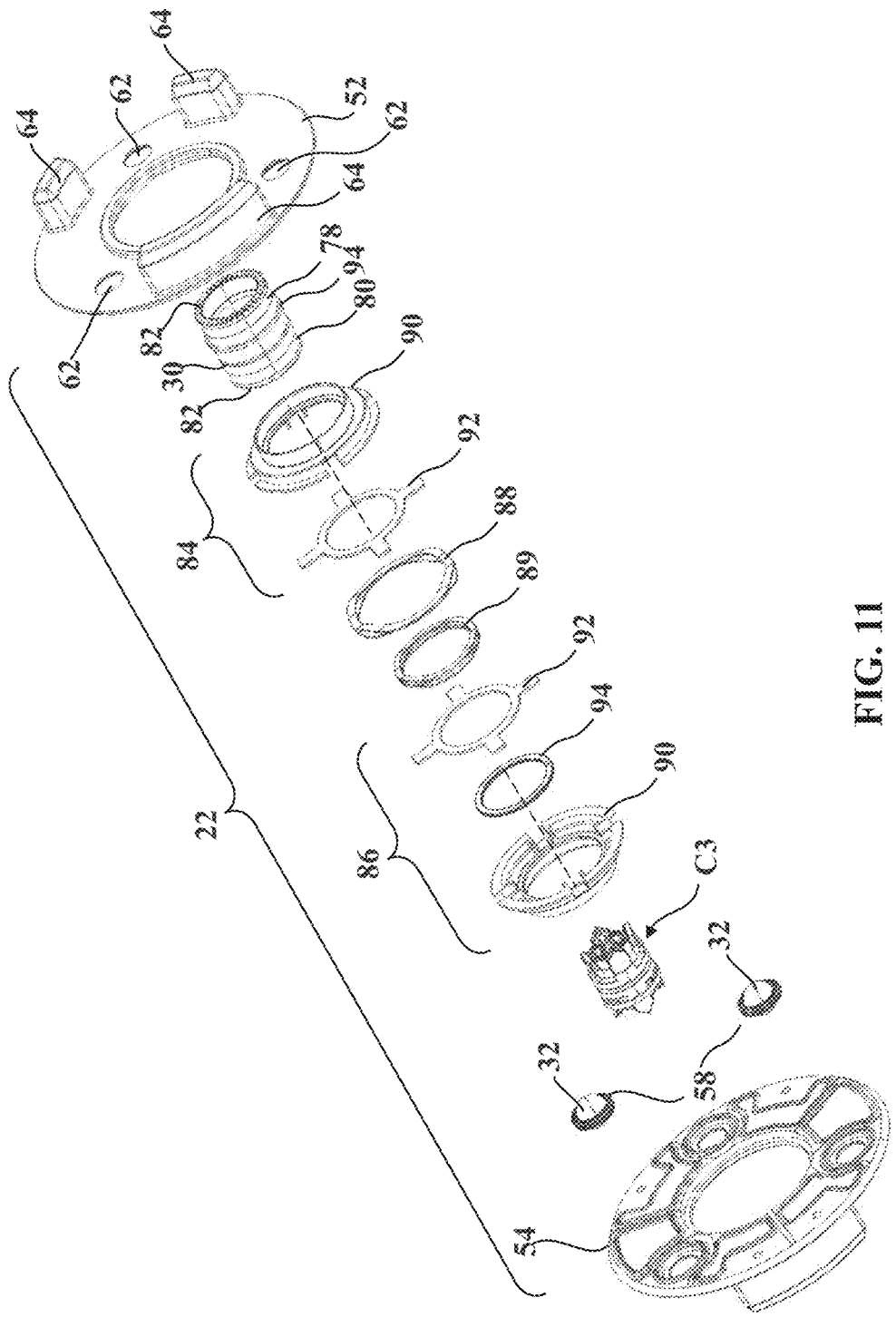
FIG. 11 is another exploded perspective view of the sterile barrier assembly of FIG. 4.
Figure 12:
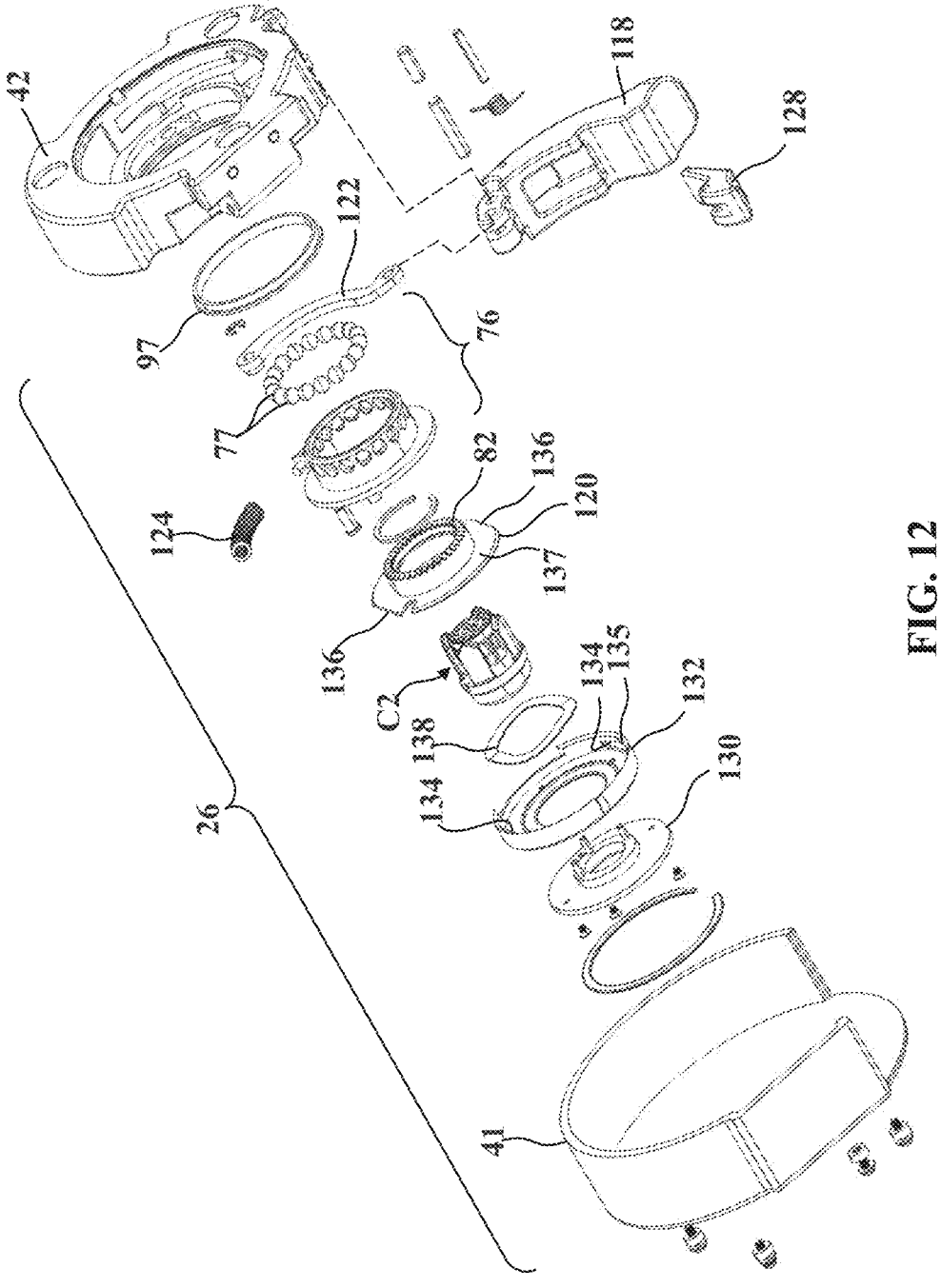
FIG. 12 is an exploded perspective view of the second mounting portion of FIG. 4 (with retainer plate omitted).
Figure 13:
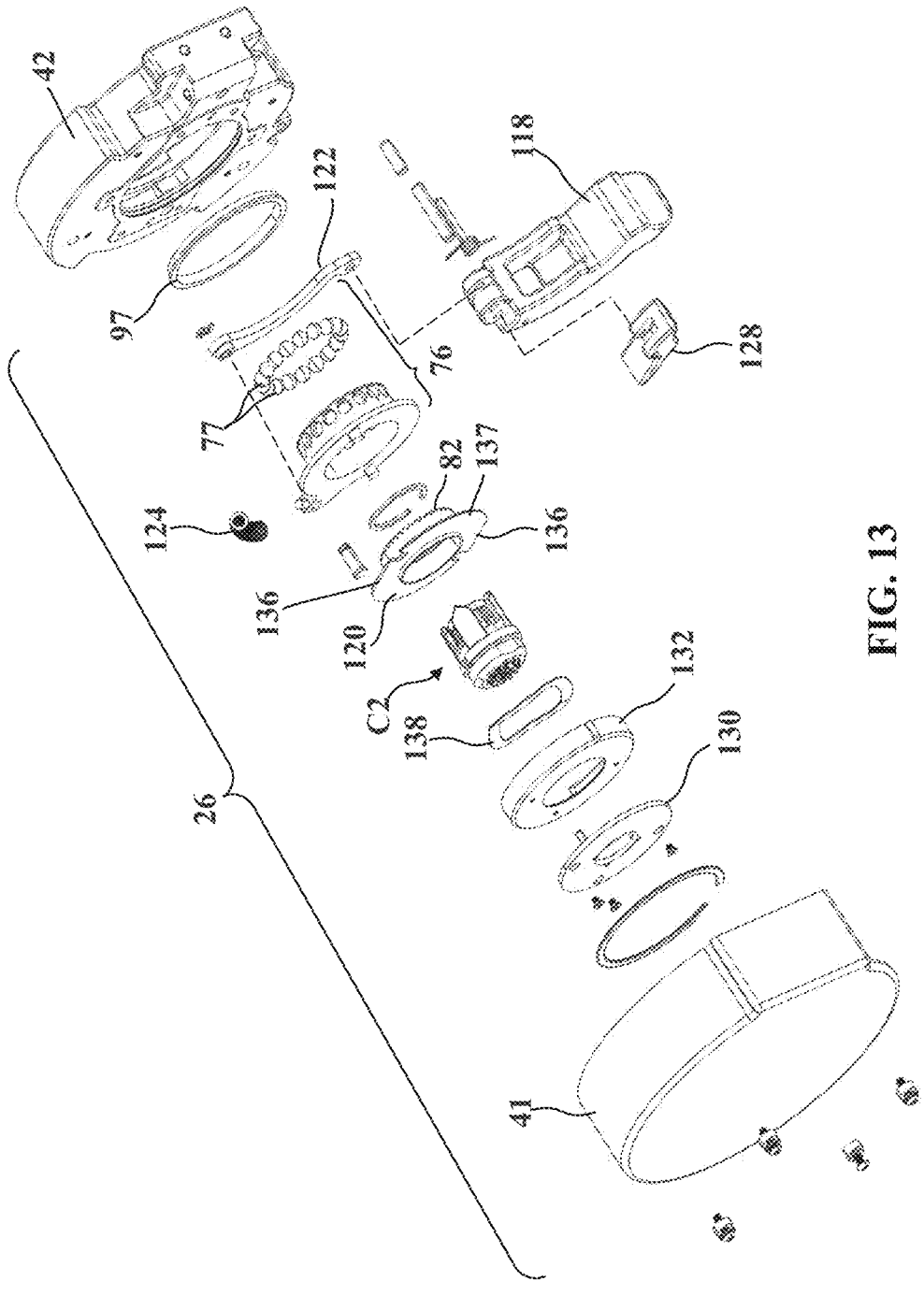
FIG. 13 is another exploded perspective view of the second mounting portion of FIG. 4 (with the retainer plate omitted).

The first and second lock assemblies comprise first and second ball subassemblies 74, 76 and first and second ball detents 78, 80 (see FIGS. 14A and 15A and also FIGS. 6, 11, and 12). The first lock assembly is interposed between the first mounting portion 24 and the coupling 30 of the sterile barrier assembly 22 to releasably secure the coupling 30 to the first mounting portion 24. Similarly, the second lock assembly is interposed between the coupling 30 and the second mounting portion 26 to releasably secure the second mounting portion 26 to the coupling 30 when the tensioner 28 is in the first position 28F. In the version shown, the ball subassemblies 74, 76 are operatively attached to the mounting portions 24, 26 and the ball detents 78, 80 are defined in the coupling 30 to receive the ball subassemblies 74, 76. Thus, the coupling 30 is configured to be disposed in communication with each of the ball subassemblies 74, 76 when the sterile barrier assembly 22 is secured to the first mounting portion 24 and the second mounting portion 26 is secured to the sterile barrier assembly 22. It will be appreciated that this configuration could be reversed such that one or both of the ball subassemblies 74, 76 could be associated with the coupling 30 and the ball detents 78, 80 associated with the mounting portions 24, 26.

Each of the lock assemblies further comprises a release collar 84, 86 (see FIG. 14A) arranged to secure one of the ball subassemblies 74, 76 received in one of the ball detents 78, 80. The release collars 84, 86 are each operatively attached to the sterile barrier assembly 22 and are biased axially away from each other. To this end, one or more biasing elements, generally indicated at 88 and 89, are provided interposed in force-translating relationship between the coupling 30 and the release collars 84, 86. In the representative example illustrated herein, the biasing elements 88, 89 are formed as stacked wave washers. Any suitable number of biasing elements 88, 89 of any suitable type, configuration, or arrangement, could be utilized.

Figure 10:
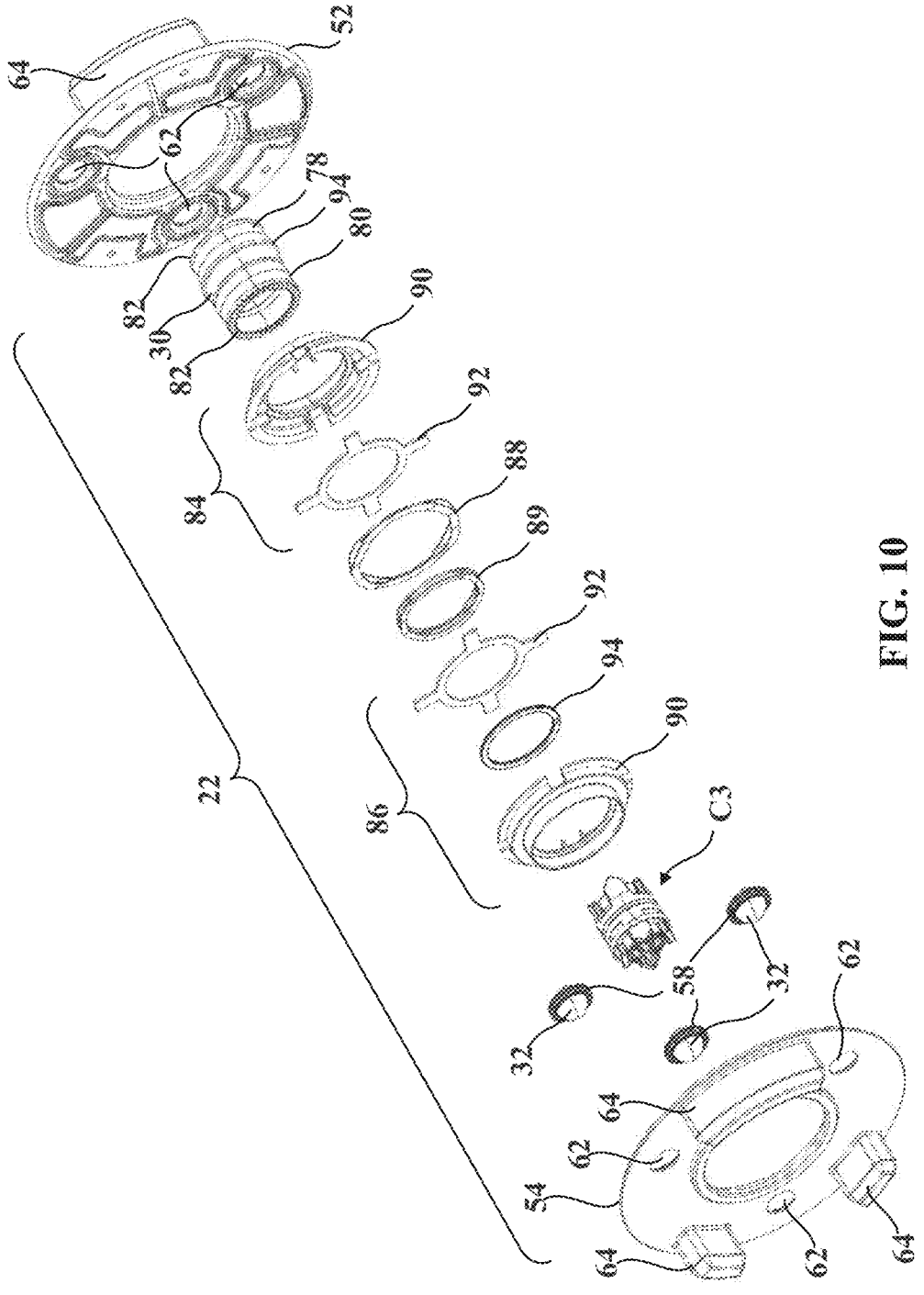
FIG. 10 is an exploded perspective view of the sterile barrier assembly of FIG. 4.

In order to facilitate assembly of the sterile barrier assembly 22, each of the release collars 84, 86 has a collar body, generally indicated at 90, and a collar keeper, generally indicated at 92, which is shaped to engage and rotate concurrently with the collar body 90 via a tab-and-pocket arrangement (see FIGS. 10 and 11). The collar keepers 92 are arranged concentrically with the respective collar bodies 90 such that a collar biasing element 88 abuts each of the collar bodies 90 and urges the collar bodies 90 axially away from each other and into abutment with the interface plates 52, 54, and keeper biasing element 89 abuts each of the collar keepers 92 and urges the collar keepers 92 axially away from each other and into abutment with a respective ring 94. Here, the rings 94 are either integral with the coupling 30 or seated in a respective groove formed in the coupling 30 and act to bias and retain the coupling 30 axially with respect to the interface plates 52, 54. It will be appreciated that this arrangement allows the coupling 30 to rotate with respect to the interface plates 52, 54. Moreover, this arrangement allows axial movement of the release collars 84, 86 with respect to the interface plates 52, 54 and/or the coupling 30, which facilitates releasable attach-ment/detachment of the sterile barrier assembly 22 to the mounting portions 24, 26 as noted above and as is described in greater detail below. In some examples, such as that shown, either side of the sterile barrier assembly 22 can be coupled to the first mounting portion 24, i.e., the sterile barrier assembly 22 could be flipped from its orientation shown in FIG. 14A and still successfully attach to the first mounting portion 24.

Referring to the progression shown from FIG. 14A through FIG. 14C, when attaching the sterile barrier assem-bly 22 to the first mounting portion 24, one end of the coupling 30 first comes into contact with the first ball subassembly 74, and more particularly, comes into contact with balls 75 of the first ball subassembly 74. When this happens, as shown in FIG. 14B, the balls 75 are urged radially outwardly in their carrier. As a result, the balls 75 engage an end of one of the collar bodies 90, and as the user applies more force onto the interface 48, the corresponding collar body 90 compresses against the biasing force of collar biasing element 88 (compare FIG. 14A to FIG. 14B). As the user continues to apply force onto the interface 48, now referring to FIG. 14C, the first ball detent 78 (e.g., a groove formed in the coupling 30) aligns with the balls 75 so that the balls 75 fit into the first ball detent 78 and the collar body 90 thereafter moves axially to a location behind the balls 78 to hold the balls 75 in the first ball detent 78. The sterile barrier assembly 22 is now releasably attached to the first mounting portion 24. Referring to FIG. 15A, similar action occurs to lock the second mounting portion 26 to the sterile barrier assembly 22 via the other release collar 86 and the second ball subassembly 76, which includes balls 77.

Referring now to FIGS. 15B through 21B, when the sterile barrier assembly 22 is secured to the first mounting portion 24 and the second mounting portion 26 is secured to the sterile barrier assembly 22, movement of the tensioner 28 from the first position 28F (see FIG. 2) towards the second position 28S (see FIG. 3) causes kinematic coupling of the end effector EE to the robotic arm R via the kinematic couplers 32 and via the preload force being applied to the mounting portions 24, 26 to securely hold the mounting portions 24, 26 together in their kinematically coupled arrangement. To this end, in one example, the first mounting portion 24 comprises a loading mechanism, generally indi-cated at 98 (see FIGS. 15B, 16A and 16B), to assist in applying the preload force. When actuated, the loading mechanism 98 urges at least one of the second mounting portion 26 and the sterile barrier assembly 22 axially towards the robotic arm R in response to movement of the tensioner 28 towards the second position 28S.

The coupling 30 of the sterile barrier assembly 22 is interposed in force-translating relationship between the ten-sioner 28 and the loading mechanism 98 such that actuation of the tensioner 28 from the first position 28F toward the second position 28S causes rotational force to be applied through the coupling 30 to the loading mechanism 98, which in turn causes the preload force to be applied through the coupling 30 to axially translate the second mounting portion 26 toward the first mounting portion 24 to securely hold the second mounting portion 26 to the first mounting portion 24 through the kinematic couplers 32 in their kinematically coupled arrangement.

In the example shown, the loading mechanism 98 is configured to move the first ball subassembly 74 axially relative to the first mounting plate 38 in response to move-ment of the tensioner 28 towards the second position 28S (compare FIG. 16A to FIG. 16B) so that the second mount-ing portion 26 is urged toward the first mounting portion 24. Accordingly, the coupling 30, which is axially locked to the first ball subassembly 74, also moves axially along with the first ball subassembly 74. Concurrently, the second ball subassembly 76, which is also axially locked to the coupling 30, also moves axially along with the first ball subassembly 74 and the coupling 30. The second ball subassembly 76 has a flange sized to axially bear against the second mounting plate 42 via a loading ring 97 such that actuation of the loading mechanism 98 draws the second mounting plate 42 toward the first mounting plate 38.

The loading mechanism 98 comprises a drive 102 and a load actuator 104. The drive 102 is operatively attached to the first ball subassembly 74. In the example shown, the drive 102 is fixed to the first ball subassembly 74, such as via a press-fit, welding, or the like. The drive 102 could also be operatively attached to the first ball subassembly 74 by being integrally formed with the first ball subassembly 74. The drive 102 is configured to be placed in rotational engagement with the coupling 30 of the sterile barrier assembly 22 when the sterile barrier assembly 22 is releas-ably attached to the first mounting portion 24. In the version shown, the drive 102 and the coupling 30 have correspond-ing spline arrangements, generally indicated at 82, which are configured to facilitate concurrent rotation about the longi-tudinal axis L1 in use. Specifically, the coupling 30 has end splines or teeth which engage corresponding end splines or teeth of the drive 102. Any suitable type of rotational engagement could be employed to facilitate rotational com-munication between the coupling 30 and the drive 102. The drive 102 is arranged such that rotation of the drive 102 about the longitudinal axis L1 causes the first ball subas-sembly 74 to move axially along the longitudinal axis L1 in a manner that applies the preload force between the first mounting portion 24 and the second mounting portion 26 in response to movement of the tensioner 28 towards the second position 28S.

Referring to FIGS. 16A-20B, the load actuator 104 com-prises a first hub 106 and a second hub 108 opposing the first hub 106. The first hub 106 is operatively attached to the first ball subassembly 74. In some examples, the first hub 106 is operatively attached to the first ball subassembly 74 by virtue of being integrally formed with the first ball subas-sembly 74. The second hub 108 is operatively attached to the first mounting plate 38. More specifically, the second hub 108 and the first mounting plate 38 have corresponding geometric shapes (e.g., corresponding flats 101, 103 shown in FIGS. 6 and 7) that inhibit relative rotation between the second hub 108 and the first mounting plate 38 but allow a small amount of axial movement between the second hub 108 and the first mounting plate 38. The amount of axial movement allowed is limited by the size of grooves in the first mounting plate 38 and the second hub 108 in which a retaining ring 105 is located. The retaining ring 105 couples the second hub 108 to the first mounting plate 38.

The load actuator 104 further comprises a plurality of ball bearings 110 arranged between the first hub 106 and the second hub 108. Ramps 112 are defined in one or more of the first hub 106 and the second hub 108. In the example shown, a first set of ramps 112 is defined in the first hub 106 and a second set of ramps 112 is defined in the second hub 108 to effectively double the axial travel between the hubs 106, 108 during actuation (as compared to using only one set of ramps), as will be described. Of course, one set of ramps could be employed. The ball bearings 110 roll along the ramps 112 in response to movement of the tensioner 28 towards the second position 28S. More specifically, in the version shown in FIGS. 17-19, the ball bearings 110 (six shown) are disposed in the opposing first and second sets of ramps 112 (six shown in each set) formed within the hubs 106, 108. In some versions, the ramps 112 have a linear ramp slope, but the ramps 112 may also have a non-linear ramp slope, or combinations of linear and non-linear ramp slopes. Non-linear ramp slopes may be advantageous, for example, to reduce sensitivities of the loading mechanism 98 to tolerance stack up.

Figures 17, 18, 19, 20A, 20B:
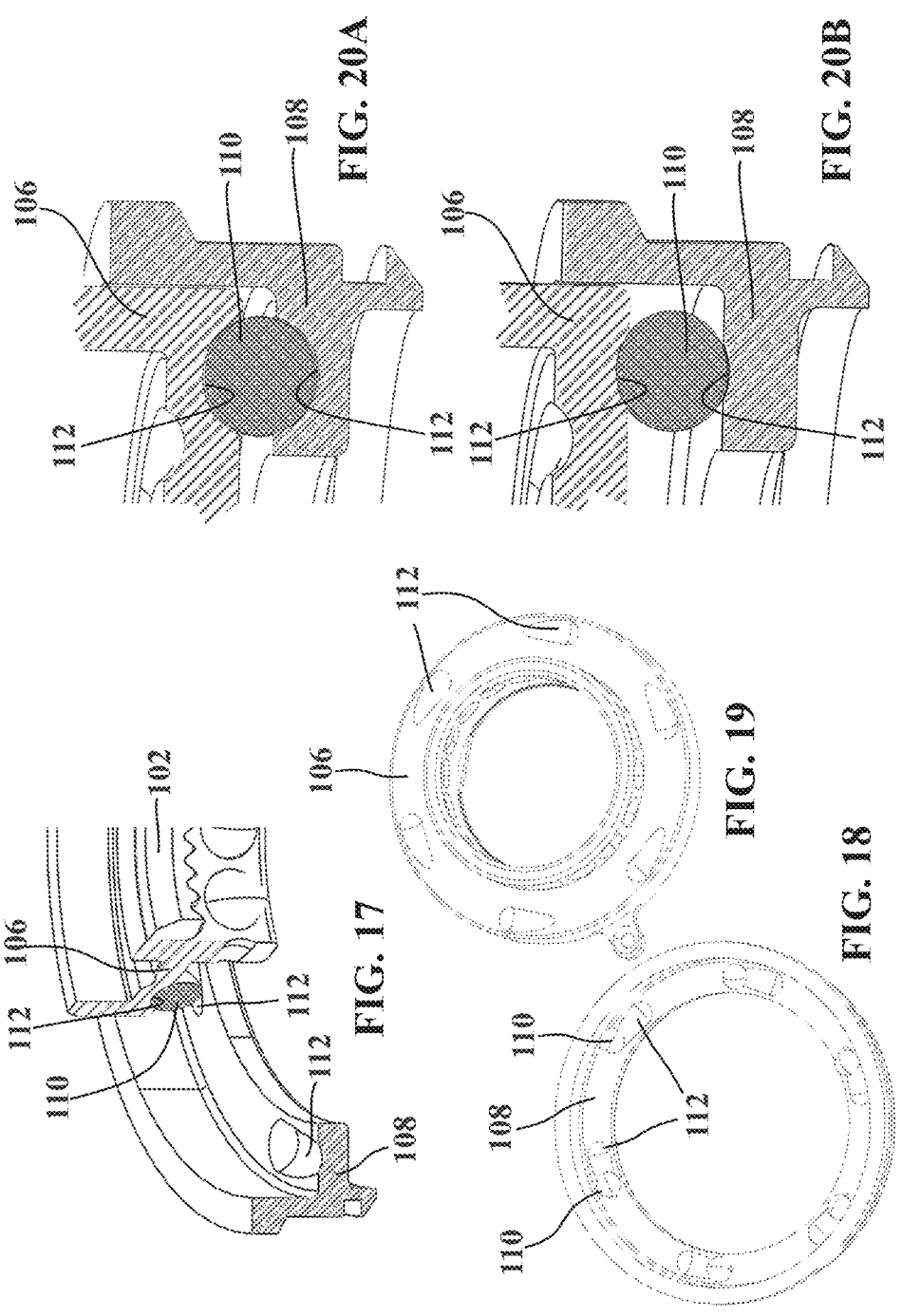
FIG. 17 is a partial perspective section view illustrating a load actuator.
FIG. 18 is a top perspective view of a second hub.
FIG. 19 is a bottom perspective view of a first hub.
FIGS. 20A and 20B are blown-up section views taken from FIGS. 16A and 16B, respectively.

The ball bearings 110 and the ramps 112 are sized and shaped so that relative rotation between the hubs 106, 108 causes the ball bearings 110 to roll along the ramps 112, wherein rotation in one direction causes the hubs 106, 108 to axially separate from one another while rotation in an opposite direction causes the hubs 106, 108 to move axially closer together (compare FIGS. 20A and 20B). A return spring 114 (e.g., one or more wave washers) acts between the first hub 106 and the hub mount 40 (see FIG. 15B) to move the hubs 106, 108 closer together when the tensioner 28 is moved back to the first position 28F. More specifically, the return spring 114 acts between the hub mount 40 and a roller bearing assembly 115 that facilitates smooth rotation of the first hub 106 relative to the second hub 108 so that the return spring 114 can more easily return the first hub 106 to its normal, unactuated position.

Referring back to FIGS. 16A and 16B, since the drive 102 is fixed to the first hub 106, rotation of the drive 102 relative to the first mounting plate 38 causes rotation of the first hub 106 relative to the first mounting plate 38 about the longitudinal axis L1. Similarly, since the second hub 108 is inhibited from rotating relative to the first mounting plate 38, rotation of the drive 102 relative to the first mounting plate 38 is also rotation of the first hub 106 relative to the second hub 108. This relative rotational movement causes the relative axial movement between the hubs 106, 108 along the longitudinal axis L1, owing to the ball bearings 110 rolling along their corresponding ramps 112, i.e., the hubs 106, 108 move axially apart when the ball bearings 110 roll up the ramps 112 and the hubs 106, 108 move axially together when the ball bearings 110 roll down the ramps 112 (compare FIGS. 16A and 16B). The ball bearings 110 are at rest at a deepest end of the ramps 112 when the tensioner 28 is in the first positions 28F. The load actuator 104 is arranged and configured so that the hubs 106, 108 move axially away from each other in response to movement of the tensioner 28 towards the second position 28S.

Figures 16A, 16B, 16C:
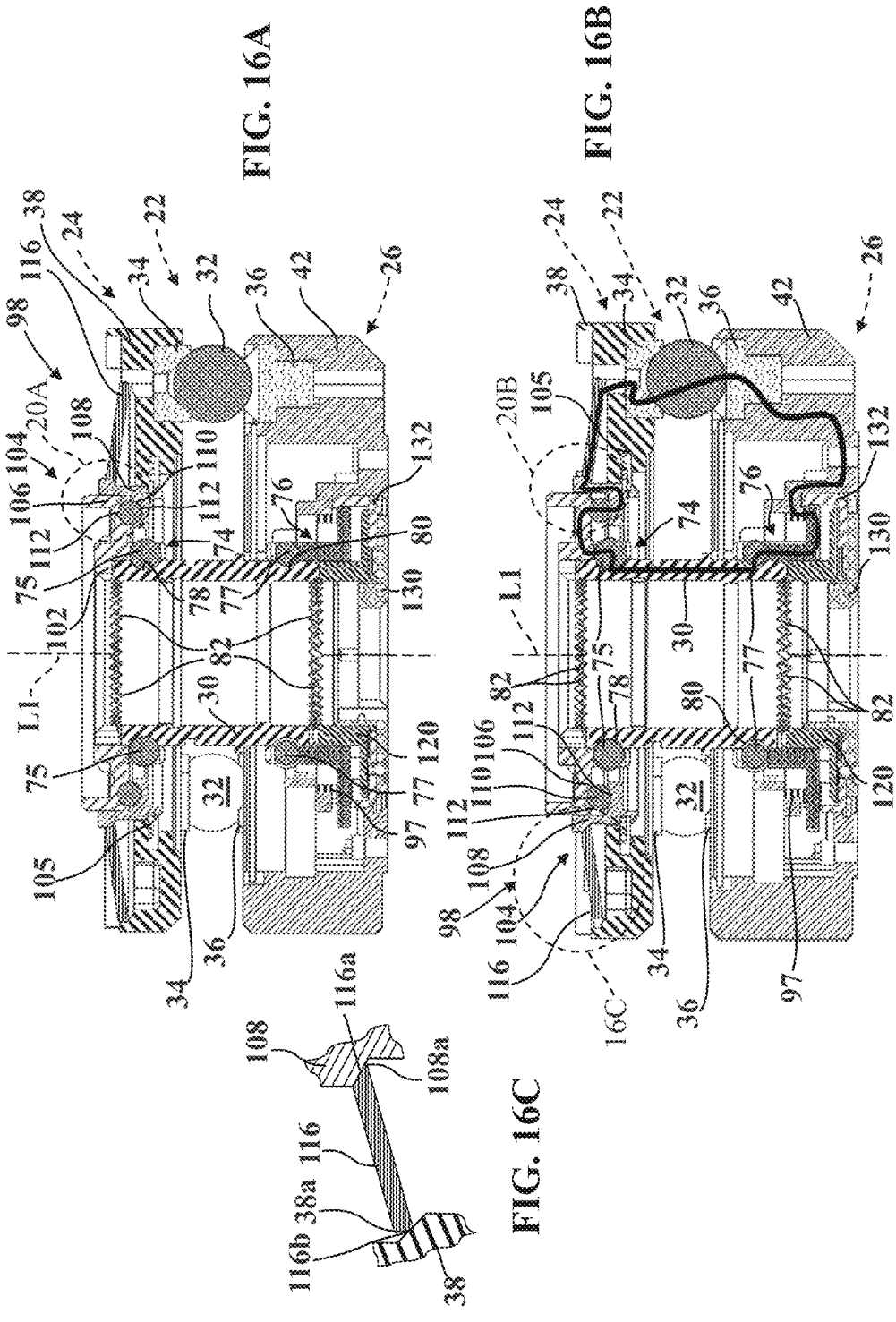
FIGS. 16A and 16B are section views taken generally along line 15B-15B in FIG. 4, except that many components have been removed for illustration purposes to show a preload force being applied to the mounting system to draw the second mounting portion toward the first mounting portion, including showing a load path of the preload force in FIG. 16B.
FIG. 16C is a blown-up view of FIG. 16B showing a biasing element.

The loading mechanism 98 further comprises a biasing element 116 arranged to act between the second hub 108 and the first mounting plate 38. The biasing element 116 comprises a conical spring washer (also referred to as a Belleville washer/spring) in the example shown. As shown in FIG. 16C, in one example, the biasing element 116 comprises inner and outer annular sides 116a, 116b. The inner side 116a abuts an angled annular face 108a of the second hub 108. The outer side 116b abuts an angled annular face 38a of the first mounting plate 38. The sides 116a, 116b may have a cross-sectional profile that is squared off, chamfered, rounded, or the like (see rounded profile in FIG. 16C). The annular faces 38a, 108a may be conical in shape. The annular faces 38a, 108a may have a cross-sectional profile that is flat, concave, convex, or the like (see flat profile in FIG. 16C). The annular faces 38a, 108a are angled from 5 to 85 degrees, from 10 to 80 degrees, from 30 to 70 degrees, from 40 to 70 degrees, or the like, relative to the longitudinal axis L1. The annular faces 38a, 108a may be arranged at the same acute angle or at different acute angles relative to the longitudinal axis L1. The arrangement of the biasing element 116, including its abutment and compression between the annular faces 38a, 108a, may cause a biasing element designed to normally exhibit a linear load vs. deflection relationship to exhibit a non-linear load vs. deflection relationship.

The biasing element 116 may comprise any suitable resilient element or spring to provide the preload force needed to suitably secure the second mounting portion 26 to the first mounting portion 24. In some examples, the biasing element 116 may comprise one or more diaphragm springs, buckling springs, or the like. Additionally, in some versions, the biasing element 116 may be slotted or have one or more openings between its inner and outer peripheries.

During use, when the loading mechanism 98 is actuated, the first hub 106 moves axially away from the second hub 108 to initially place the kinematic couplers 32 into better contact with the receptacles 34, 36 of the mounting plates 38, 42 by taking up slack between the mounting plates 38, 42 (compare FIGS. 16A and 16B). Once the kinematic couplers 32 are secured in the receptacles 34, 36 and make the desired contact with the surfaces of the receptacles 34, 36, then the mounting plates 38, 42 are at their desired relative positions and cannot be further drawn together owing to the rigid nature of the kinematic couplers 32 and the receptacles 34, 36, which are rigidly fixed to the mounting plates 38, 42, all of which may be formed of metal. As a result, further actuation of the loading mechanism 98, i.e., further rotation of the drive 102, will now axially move the second hub 108 away from the first hub 106. This is a result of the first hub 106 being axially fixed from movement since the mounting plates 38, 42 are no longer axially moving toward one another. Accordingly, since the second hub 108 is in contact with the biasing element 116, further actuation of the loading mechanism 98 causes compression of the biasing element 116. As a result, the biasing element 116 provides resistance to define the preload force or at least a portion of the preload force that hold the mounting portions 24, 26 together. The biasing element 116 acts between the second hub 108 and the first mounting plate 38 and continuously engages the second hub 108 and the first mounting plate 38 throughout movement of the tensioner 28.

In one example, the conical spring washer provides from 200 lbs to 500 lbs of preload force, from 350 lbs to 450 lbs of preload force, or about 400 lbs of preload force. The conical spring washer may have a non-linear relationship of compression distance to preload force such that axial compression of the conical spring washer of 2 millimeters or less may result in a change in the preload force of only about +/−10%. As a result, a consistent preload force can be applied regardless of tolerances in assembly of the loading mechanism 98 or other components and so that a consistent preload force can be expected by users during each use.

Figures 21A, 21B:
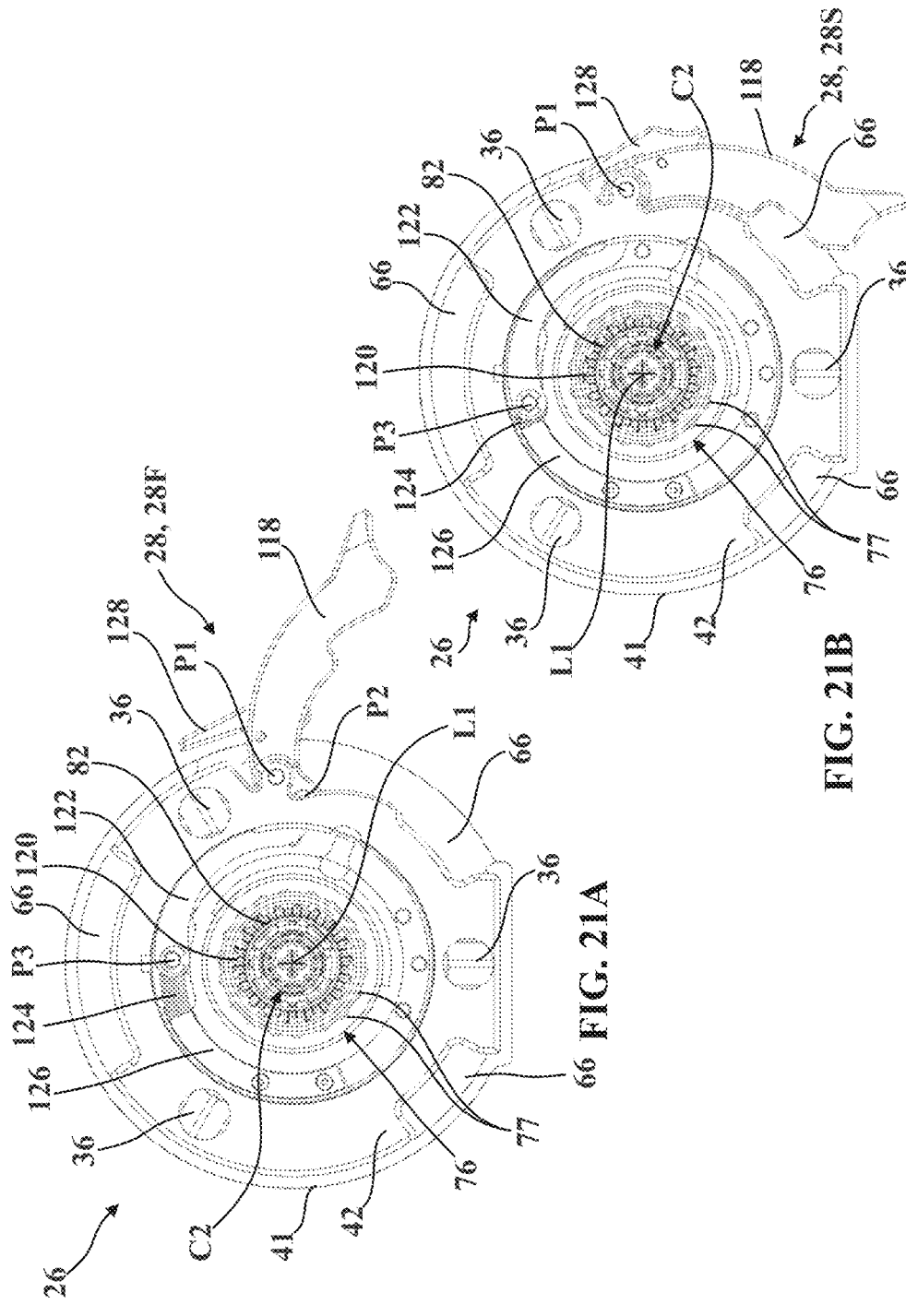
FIG. 21A is a plan view of the second mounting portion illustrating a tensioner comprising a lever and an activator link in a first, open position.
FIG. 21B is a plan view of the second mounting portion illustrating the tensioner in a second, closed position.
Figures 22, 23:
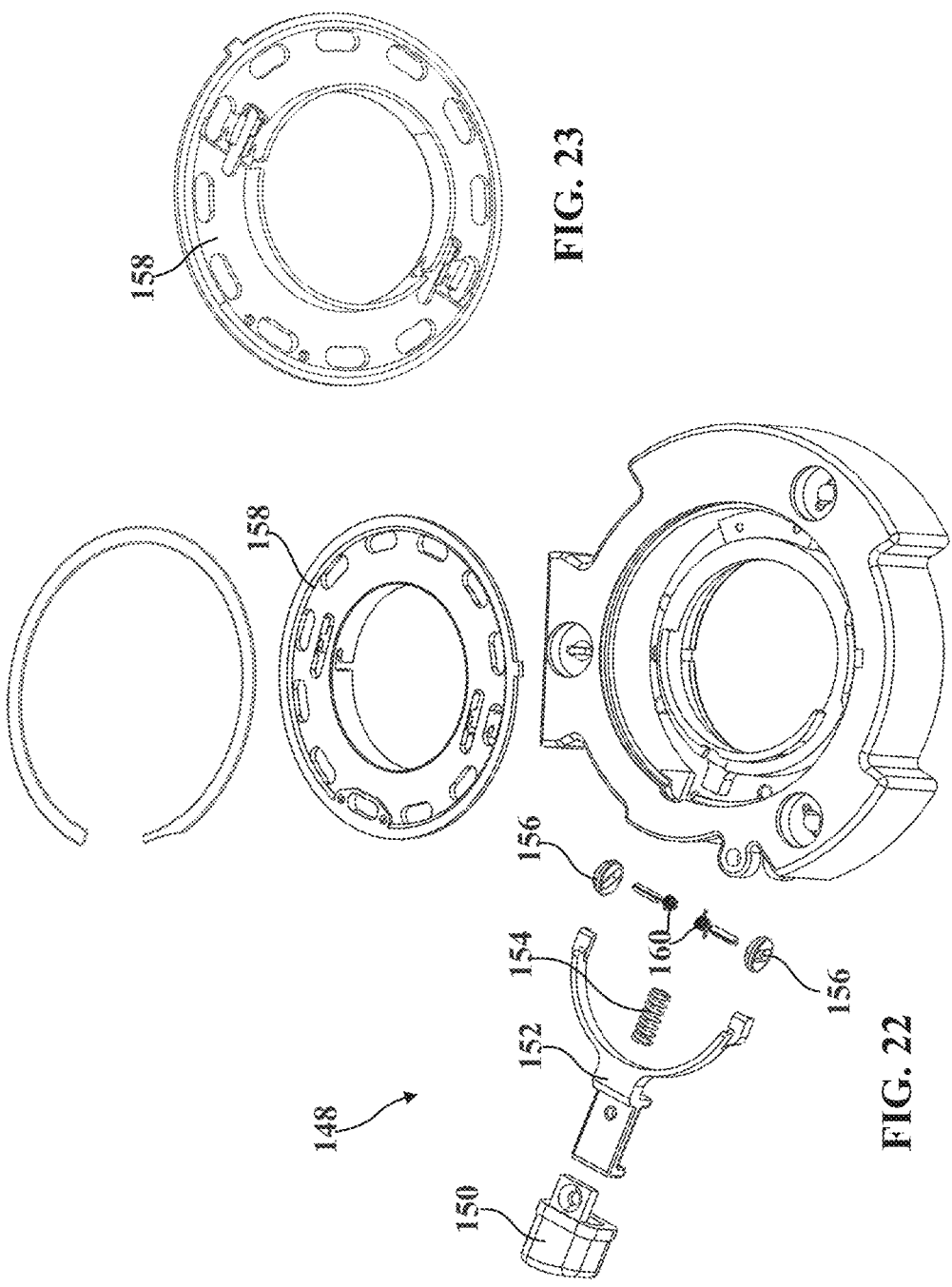
FIG. 22 is an exploded perspective view of a release mechanism of the second mounting portion.
FIG. 23 is a bottom perspective view of a retainer plate of the release mechanism.

Referring to FIGS. 21A and 21B, the tensioner 28 comprises a lever 118 (also referred to as a handle), an activator 120, and an activator link 122 interposed in force-translating relationship between the lever 118 and the activator 120 such that when the second mounting portion 26 is releasably secured to the coupling 30 (coupling 30 not shown in FIGS. 21A, 21B), movement of the tensioner 28 from the first position 28F (FIG. 21A) to the second position 28S (FIG. 21B) causes rotation of the activator 120 about the longitudinal axis L1 for concurrent rotation of the coupling 30 and the drive 102 about the longitudinal axis L1 to apply the preload force.

The lever 118 extends outwardly from the second mounting plate 42 in the first position (FIG. 21A) and nests against the second mounting plate 42 in the second position (FIG. 21B). The lever 118 is pivotally connected to the second mounting plate 42 to pivot at a first pivot joint P1 about a first pivot axis normal to the second mounting plate 42. The lever 118 is further pivotally connected to the activator link 122 to pivot at a second pivot joint P2 about a second pivot axis parallel to the first pivot axis. The activator link 122 is pivotally connected to the activator 120 to pivot at a third pivot joint P3 about a third pivot axis parallel to the first and second pivot axes.

As the lever 118 is rotated/pivoted from the first position 28F to the second position 28S about the first pivot axis, the activator link 122 is urged to rotate (e.g., counterclockwise in the plan view shown in FIGS. 21A, 21B), which thereby rotates the activator 120 (again counterclockwise). The arrangement of pivot joints P1, P2, P3 between the lever 118 and the second mounting plate 42, between the lever 118 and the activator link 122, and between the activator link 122 and the activator 120 affords mechanical advantage to the tensioner 28. The pivot joints P1, P2, P3 may be formed by connecting pins, shafts, and the like. The loading mechanism 98 and the tensioner 28 may be configured to limit relatively high forces required to be exerted by the user on the lever 118 and to maximize travel of the lever 118 during relatively low forces.

A biasing element 124, such as a compression spring, acts between a spring block 126 fixed to the second mounting plate 42 and the activator 120 to bias the tensioner 28 towards the first position 28F until the tensioner 28 is subsequently moved to the second position 28S so as to effect kinematic coupling of the end effector EE. A lever lock 128 is operatively coupled to the lever 118 (e.g., via a pivot connection) to lock the lever 118 to the second mounting portion 26 when the tensioner 28 is in the second position 28S (see FIG. 21B).

Referring briefly back to FIGS. 15A and 15B, the activator 120 is seated for selective rotational motion within the second mounting plate 42. More specifically, the activator 120 is disposed between a centering member 130 (e.g., centering plate) and a rotational lock plate 132. The centering member 130 and the lock plate 132 are fixed to the second mounting plate 42 so that when the activator 120 is actuated for rotation via the lever 118, the activator 120 rotates about the longitudinal axis L1 relative to the centering member 130 and the lock plate 132.

The lock plate 132 is arranged and configured so that the activator 120 is unable to rotate when the second mounting portion 26 is disconnected from the sterile barrier assembly 22. In other words, once the lever 118 has been moved back to the first position 28F and the second mounting portion 26 removed from the sterile barrier assembly 22, the lever 118 is unable to be rotated to the second position 28S by virtue of interference between the activator 120 and the lock plate 132. This facilitates cleaning of the second mounting portion 26 via autoclave, for example, by keeping the lever 118 open and allowing the cleaning agent (e.g., steam) to penetrate into the internal components of the second mounting portion 26. Additionally, this also prevents users from trying to place the second mounting portion 26 onto the sterile barrier assembly 22 with the lever 118 in the closed, second position 28S, which is not possible, and could otherwise confuse or frustrate the user.

The activator 120 is inhibited from rotating relative to the lock plate 132 and the second mounting plate 42 by virtue of flats 134 of the lock plate 132 being axially aligned with flats 136 of the activator 120 in a rotationally locked position (see FIGS. 12 and 15A). The flats 134 are located on flanges 135 of the lock plate 132 and the flats 136 are located on a flange 137 of the activator 120. In an unlocked position, the activator 120 is able to rotate relative to the lock plate 132 and the second mounting plate 42 by virtue of the flats 134, 136 being axially offset. A biasing element 138 (e.g., a wave spring) biases the activator 120 toward the locked position.

The activator 120 is arranged to engage the coupling 30 when securing the second mounting portion 26 to the sterile barrier assembly 22 such that the coupling 30 urges the activator 120 into the unlocked position when the connection between the sterile barrier assembly 22 and the second mounting portion 26 is made via the second lock assembly. In particular, the coupling 30 axially engages the activator 120 so that the flange 137 of the activator 120 is axially moved to a location beneath the flanges 135 of the lock plate 132 such that the flats 134, 136 are no longer in an abutting and interfering relationship (compare FIG. 15A to FIG. 15B). Once unlocked, the activator 120 is able to rotate in response to movement of the tensioner 28 towards the second position 28S such that the activator 120, the coupling 30, the drive 102, and the first hub 106 rotate concurrently relative to the mounting plates 38, 42 to apply the preload force.

The activator 120 is arranged to be placed in rotational engagement with the coupling 30 of the sterile barrier assembly 22 when the second mounting portion 26 is releasably secured to the coupling 30. To this end, the coupling 30 and the activator 104 have corresponding spline arrangements, generally indicated at 82 (see FIG. 15A), which are configured to facilitate concurrent rotation about the longitudinal axis L1 in use. Specifically, the coupling 30 has end splines or teeth which engage corresponding end splines or teeth of the activator 120. However, any suitable type of rotational engagement could be employed to facilitate rotational communication between the coupling 30 and the activator 120.

The first mounting portion 24 may comprise electronics needed for carrying out certain functions of the surgical components. In one version, referring to FIGS. 7 and 8, a Hall effect sensor 140 (see FIG. 8) may be carried by a printed circuit board PCB fixed to the mounting hub 40. A corresponding magnet 142 (see FIG. 7) is carried by the first hub 106 to rotate with the first hub 106. Alternatively, a sensor may be carried by the first hub 106 to move relative to a magnet fixed on the printed circuit board PCB. The sensor 140 is coupled to a controller 144, which may be located on the printed circuit board PCB, or located elsewhere to receive appropriate signals from the sensor 140. The sensor 140 is arranged to cooperate with the magnet 142 to generate signals indicative of the amount of rotation of the first hub 106 relative to the hub mount 40 and the first mounting plate 38. This provides the controller 144 with information about whether the second mounting portion 26 is appropriately secured to the first mounting portion 24. In one example, the controller 144 monitors rotation via the sensor 140 to determine if the first hub 106 has rotated at least a predetermined amount, such as at least 10 degrees, at least 20 degrees, at least 30 degrees, or the like. One or more windows or grooves 146 (see FIG. 8) may be formed in a bottom wall of the hub mount 140 to facilitate reading movement of the magnet 142 via the sensor 140 through the bottom wall.

Referring to FIGS. 22 through 25B, the second mounting portion 26 comprises a release mechanism 148 operable to move one or more of the release collars 84, 86 (refer to FIG.

15B) to release the second mounting portion 26 from the coupling 30 after the lever 118 of the tensioner 28 has been opened to the first position 28F. The release mechanism 148 comprises a release actuator 150, a release link 152, a biasing element 154 (e.g., compression spring), and one or more release elements 156. The one or more release elements 156 are operatively arranged between the release actuator 150 and the one or more of the release collars 84, 86 such that actuation of the release actuator 150 moves the release link 152 against the bias of the biasing element 154 to displace the one or more of the release collars 84, 86 and allow one or more of the ball subassemblies 74, 76 to be released from one or more of the ball detents 78, 80. In the version shown, the release mechanism 148 operates to move the second release collar 86 to release the second ball subassembly 76 from the second ball detent 80.

Figures 24A, 24B:
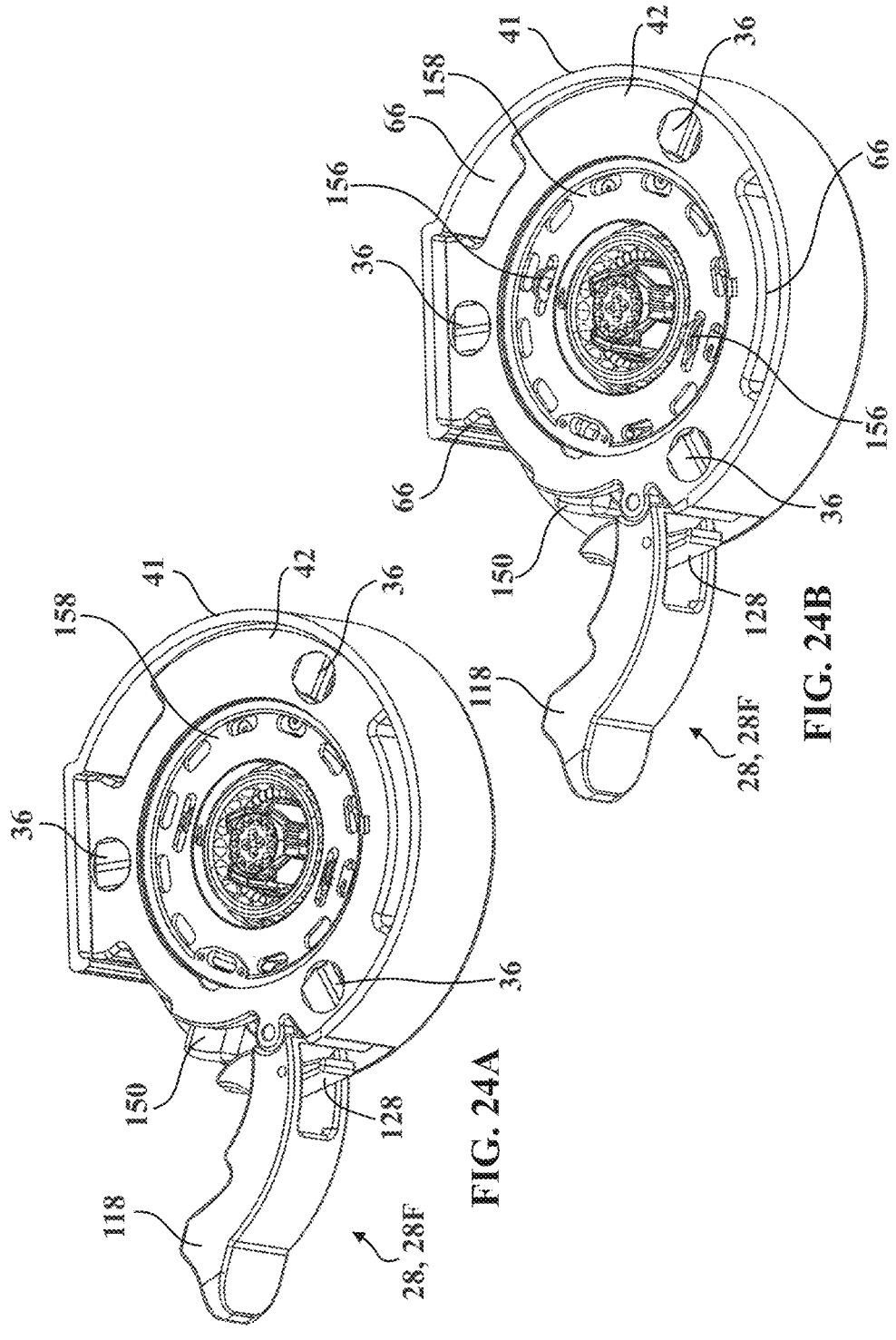
FIGS. 24A and 24B are perspective views of the second mounting portion illustrating a release actuator of the release mechanism moving from a first position to a second position.

Referring to FIGS. 24A and 24B, the release actuator 150 is located such that movement of the lever 118 to the second position 28S at least partially covers the release actuator 150 so that the release actuator 150 is generally inaccessible to the user when the lever 118 is in the second position 28S. When the lever 118 is opened to the first position 28F, the release actuator 150 is accessible and can be actuated by the user. In the version shown, the release actuator 150 is in the form of a push-button actuator, configured to be depressed by the user to release the second mounting portion 26 from the sterile barrier assembly 22, but any suitable form of actuator could be employed. In this version, when the release actuator 150 is depressed (compare FIG. 24A to FIG. 24B), the one or more release elements 156 project through a retainer plate 158 fixed to the second mounting plate 42 to engage the second release collar 86 and move the second release collar 86 so that the second mounting portion 26 can be removed from the sterile barrier assembly 22. When the release actuator 150 is undepressed, the one or more release elements 156 are biased via their own biasing elements 160 (e.g., torsion springs shown in FIG. 22) back beneath the retainer plate 158. Thus, the release elements 156 are arranged for movement relative to the second mounting plate 42 and the retainer plate 158 between a first, non-projecting position and a second, projecting position.

Figures 25A, 25B, 25C:
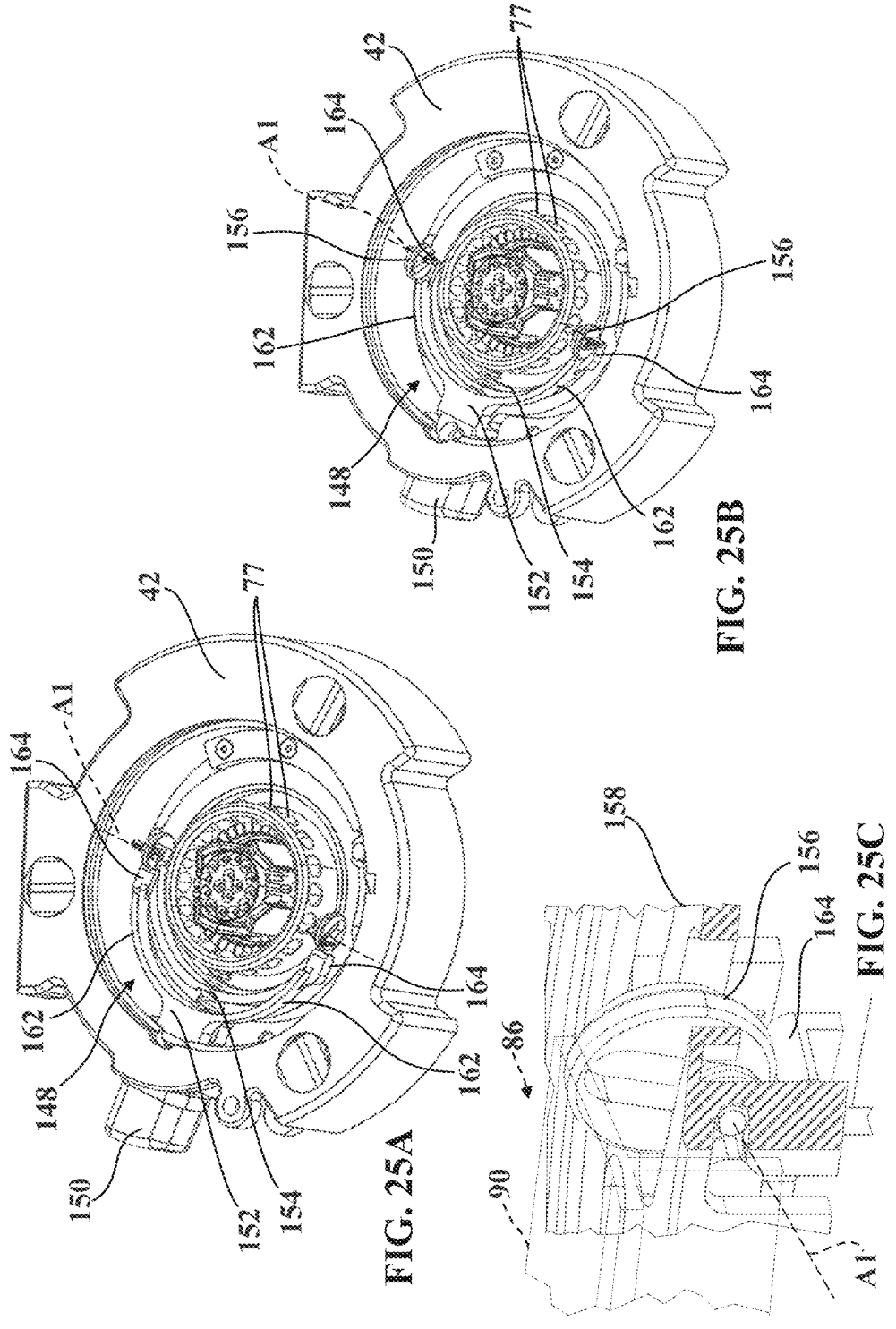
FIGS. 25A and 25B are perspective views illustrating the release actuator of the release mechanism moving from the first position to the second position to move a release link and release elements so that the second mounting portion can be removed from the sterile barrier assembly.
FIG. 25C is a partial perspective section view illustrating actuation of one of the release elements.

As shown in FIGS. 25A-25C (lever removed for clarity), the release link 152 is configured to engage the one or more release elements 156 to move the one or more release elements 156 to their second position in response to actuation of the release actuator 150. More specifically, the release link 152 comprises a pair of release arms 162, each having a cam-engaging end 164. As the cam-engaging ends 164 slide relative to the second mounting portion 42, the cam-engaging ends 164 engage the release elements 156 (see FIG. 25C). In this version, the release elements 156 are in the form of cam discs that are eccentrically mounted to the retainer plate 158 to rotate about an eccentric axis A1. The cam-engaging ends 164 are spaced relative to the eccentric axis A1 and the cam discs such that as the cam-engaging ends 164 abut the cam discs, the cam discs rotate about the eccentric axis A1 to protrude through slots in the retainer plate 158 to project beyond the retainer plate 158 to engage the second release collar 86, e.g., the collar body 90 thereof, and lift the collar body 90 until the balls 77 of the second ball subassembly 76 are able to be pulled out of the detent pocket 80 (compare to FIG. 15B showing the collar body 90 resting on the retainer plate 158).

In certain situations, it may be necessary to activate the release actuator 150 while the lever 118 is in the second position 28S (e.g., closed). This may be desired, for example, when the lever 118 is stuck in the second position

28S, such as may occur when the second mounting portion 26 is attached to the sterile barrier assembly 22, prior to coupling the sterile barrier assembly 22 to the first mounting portion 24. To this end, the lever lock 128 is arranged such that prying of the lever lock 128 with an elongated tool (screwdriver, etc.) will cause the lever lock 128 to pivot and a rear portion of the lever lock 128 will engage the release actuator 150 to move the second release collar 86, as described above. FIG. 24A shows the proximity of the rear portion of the lever lock 128 to the release actuator 150 that enables this action. Prying on the lever lock 128 as described would release the second release collar 86 and allow the second mounting portion 26 to be released from the sterile barrier assembly 22, thereby allowing the lever 118 to be moved back to the first position 28F (e.g., the open position). Another option would be to include through holes in the second mounting portion 26 that direct an elongated tool to the second release collar 86 so that the second release collar 86 can be manually moved with the elongated tool to release the sterile barrier assembly 22 from the second mounting portion 26.

In use, the sterile barrier assembly 22 is first secured to the first mounting portion 24 associated with the robotic arm R. To this end, axial movement of the coupler 30 towards the robotic arm R brings the first ball detent 78 into engagement with the balls 75 of the first ball subassembly 74 such that the first lock assembly holds the sterile barrier assembly 22 onto the first mounting portion 24, with the kinematic couplers 32 loosely seated in the first plurality of receptacles 34. Next, the drape 50 can be positioned about the robotic arm R to facilitate subsequent operation within the sterile field S. Next, axial movement of the second mounting portion 26 and the associated end effector EE, towards the secured sterile barrier assembly 22 brings the second ball detent 80 into engagement with the balls 77 of the second ball subassembly 76 such that the second lock assembly holds the second mounting portion 26 onto the sterile barrier assembly 22, with the second plurality of receptacles 36 loosely seated on the kinematic couplers 32.

The tensioner 28 of the second mounting portion 26 is biased towards the first position 28F by the biasing element 124 until the tensioner 28 is subsequently moved to the second position 28S so as to effect kinematic coupling of the end effector EE on the robotic arm R. As the tensioner 28 moves towards the second position 28S, the activator 120 rotates the coupling 30, which rotates the drive 102 via the spline arrangements 82. This rotation activates the loading mechanism 98, axially separates the hubs 106, 108 to draw the first and second mounting portions 24, 26 together and causes kinematic coupling once the tensioner 28 moves into the second position 28S. Here, the end effector EE is kinematically coupled to the robotic arm R and can be used within the sterile field S.

If the end effector EE needs to be replaced or exchanged within the sterile fields S during a procedure, the second mounting portion 26 can be removed from the sterile barrier assembly 22 without allowing contaminants to pass from or towards the robotic arm R across the sterile barrier assembly 22. Here, in order to remove the second mounting portion 26, the tensioner 28 can be moved out of the second position 28S to disengage the kinematic coupling. While the tensioner 28 is moved back to the first position 28F, the second lock assembly keeps the second mounting portion 26 secured to the sterile barrier assembly 22 which, in turn, remains secured to the first mounting portion 24 by the first lock assembly. In order to release the second mounting portion 26 from the sterile barrier assembly 22, the tensioner 28 can be moved from the first position 28F to reveal the release actuator 150, which can be depressed to cause the release elements 156 to engage the second release collar 86 which releases the second lock assembly such that the balls 77 of the second ball subassembly 76 can be withdrawn from the second ball detent 80 of the coupler 30. More specifically, axial force applied by the release elements 156 pushes the second release collar 86 axially away from the second ball subassembly 76 until the second release collar 86 no longer constrains the balls 77 of the second ball subassembly 76 in the second ball detent 80. At this point, the second mounting portion 26, and the end effector EE with which it is connected, can be removed and a different second mounting portion and second end effector, can be subsequently re-secured to the sterile barrier assembly 22.

In order to remove the sterile barrier assembly 22 from the first mounting portion 24, such as after surgery has been completed, the second mounting portion 26 and associated end effector EE are first removed from the sterile barrier assembly 22 as described above. Next, in order to remove the sterile barrier assembly 22 from the first mounting portion 24, the interface 48 can be pulled axially away from the first mounting portion 24 by the user to disengage the first lock assembly. Here, axial force applied to the interface 48 causes the first release collar 84 to move axially with respect to the coupling 30, against the bias of biasing elements 88, 89, which releases the first lock assembly such that the first ball detent 78 of the coupler 30 can be withdrawn from the first ball subassembly 74 of the first mounting portion 24. More specifically, the user applies the axial force by grasping about a periphery of the interface 48 which, in turn, pulls the first release collar 84 (both collar body 90 and collar keeper 92) axially away from the first ball subassembly 74 until the first release collar 84 no longer constrains the balls 75 of the first ball subassembly 74 in the first ball detent 78.

I. Illumination for Mounting System

Referring to FIGS. 26-29, the robotic surgical system 200 comprising the robotic arm R and the end effector EE are utilized with an illumination system to aide a user in properly mounting one or more parts of the mounting systems described herein. More specifically, the robotic surgical system 200 may comprise an illumination device 202 that is configured to emit light and change the light emission between at least a first illumination state S1 (see FIG. 28) and a second illumination state S2 (see FIG. 29).

In the example shown in FIGS. 26-29, the illumination device 202 is coupled to the robotic arm R. More specifically, the robotic arm R, and more specifically, any links of the arm disposed between robot joints, have an exterior surface 206, with the illumination device 202 disposed on or in the exterior surface 206. The illumination device 202 may have an annular configuration that encircles the exterior surface 206. Said differently, the illumination device 202 is configured like a ring that is wrapped around the exterior surface 206 and coaxial with the robot joint axis so that it can easily be visible to the user in any pose of the arm R. As shown in the Figures, the illumination device 202 may be flush (or integral) with the exterior surface 206. However, the illumination device 202 may protrude above or extend below the exterior surface 206 of the robotic arm R.

In the example shown in FIGS. 26-29, the illumination device 202 is adjacent to the first mounting portion 24, near a distal end of the robotic arm R such that the illumination device 202 is readily visible to a user operating the end effector EE. However, the illumination device 202 may be disposed anywhere along robotic arm R, including on the second mounting portion 26. Furthermore, other examples are contemplated in which the illumination device 202 is coupled to the end effector EE, the sterile barrier assembly 22, or any other suitable portion of the robotic surgical system 200. Moreover, the illumination device 202 may be spaced from the robotic arm R, the end effector EE, and the sterile barrier assembly 22. Said differently, the illumination device 202 may be a separate component that is within view of the user during use of the robotic surgical system 200. Furthermore, any number of illumination devices 202 may be utilized, which may have similar or different shapes or configurations from one another. For example, the various illumination devices 202 may be positioned at different joints of the robot arm R.

The illumination device 202 may comprise any suitable light source for emitting light visible to the user. For example, the illumination device 202 may comprise an array of LEDs or OLEDs, a display device (e.g., LCD screen) the display contents of which are controlled by software, fiber optic, or any other type of suitable technology. The LEDs or OLEDs can emit light within an entirely visible range, or a combination of infrared or visible wavelength range, and can produce any color within the visible range.

The robotic surgical system 200 may further comprise one or more controllers 204 (herein referred to as the controller 204 for simplicity) in communication with or otherwise coupled to the illumination device 202 and configured to receive a signal from another electronic or electrical component or sensor (as will be described below) to determine how to control the illumination device 202. The controller 204 is configured to control the illumination device 202 to change between the first and second illumination states S1, S2 in response to variation in the signal. The controller 204, or any ancillary components thereof, can be coupled to any one or more of the following: the end effector EE, the robot arm, the robot base, any component of the mounting system 20, including the first and second mounting portions 24, 26 or sterile barrier assembly 22, or integrated in the illumination device 202. In one example, the controller 204 may encompass, be the same as, or otherwise communicate with the controller 144 located in the first mounting portion 24, as described above.

The controller 204 may comprise or otherwise communicate with any part of the surgical system besides the illumination device 202, including any one or more of a robotic control system, a navigation system, and a tool control system which cooperate to facilitate positioning, moving, and/or driving the end effector EE relative to a target site and other parts of the robotic surgical system 200 via the arm R of the robotic system. The controller 204 can be like that described in U.S. Pat. No. 10,327,849, entitled "Robotic System and Method for Backdriving the Same" the disclosure of which is hereby incorporated by reference in its entirety. The controller 204 may be realized as or with various arrangements of computers, processors, control units, and the like, and may comprise discrete components or may be integrated (e.g., sharing hardware, software, inputs, outputs, and the like). Furthermore, the controller 204 can be realized with any suitable hardware, including a computer with a processor (e.g., a central processing unit) and/or other processors, memory, and/or storage (not shown), and loaded with software that can function as described in greater detail below. The processors can include one or more processors to control operation of the robot, the navigation system, or the end effector EE. The processors can be any type of microprocessor, multi-processor, and/or multi-core processing system. The controller 204 may additionally or alternatively comprise one or more microcontrollers, field programmable gate arrays, systems on a chip, discrete circuitry, and/or other suitable hardware, software, and/or firmware capable of carrying out the functions described herein. The term "processor" is not intended to limit any embodiment to a single processor. The controller 204 may also comprise, define, or otherwise employ a user interface with one or more output devices (e.g., screens, displays, status indicators, and the like) and/or input devices (e.g., push button, keyboard, mouse, microphone, voice-activation devices, gesture control devices, touchscreens, foot pedals, pendants, and the like). Other configurations are contemplated.

Figures 26, 27:
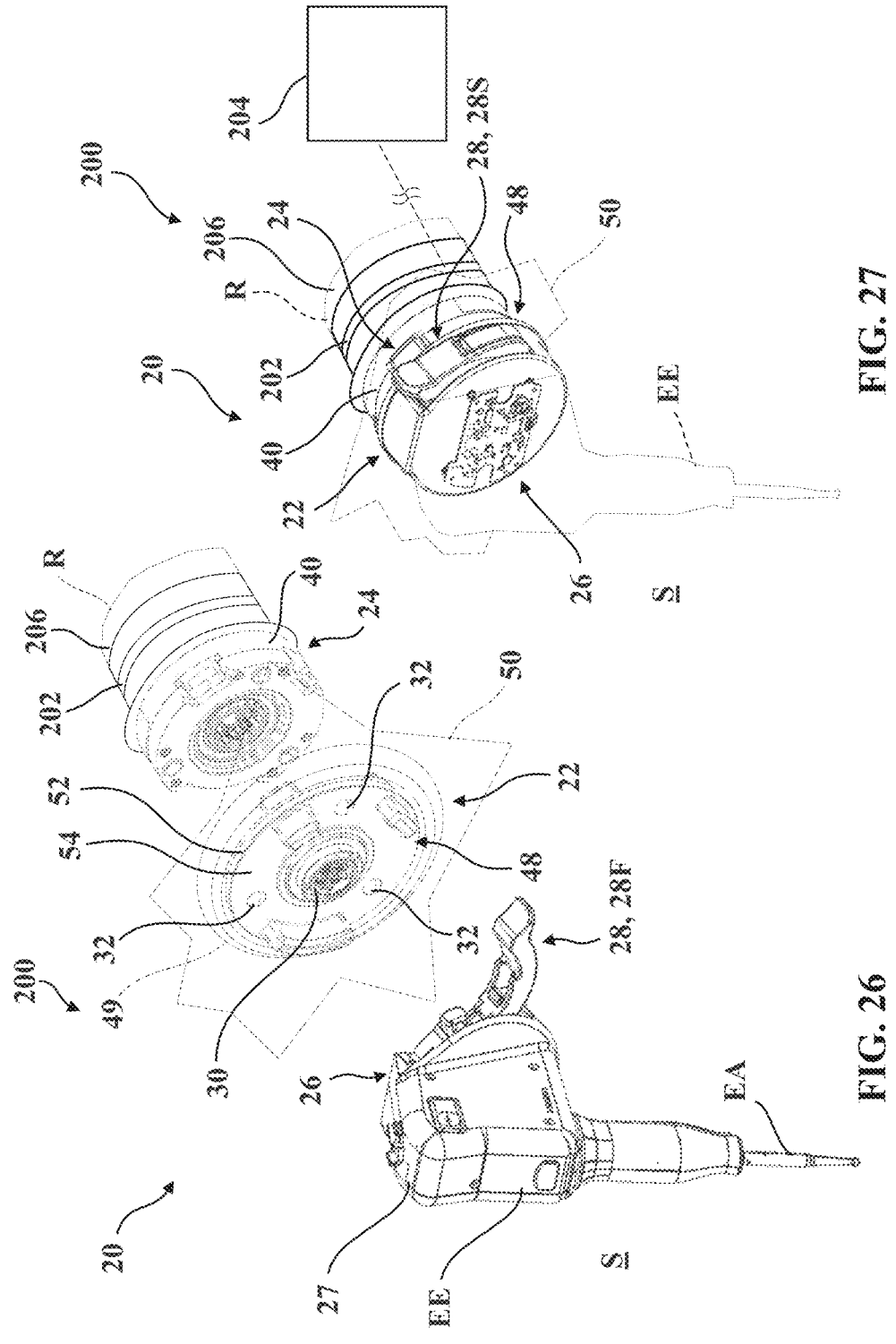
FIG. 26 is a partially exploded perspective view of a robotic surgical system having the mounting system and showing an illumination device.
FIG. 27 is a perspective view of the robotic surgical system of FIG. 26 showing the illumination device.
Figures 28, 29:
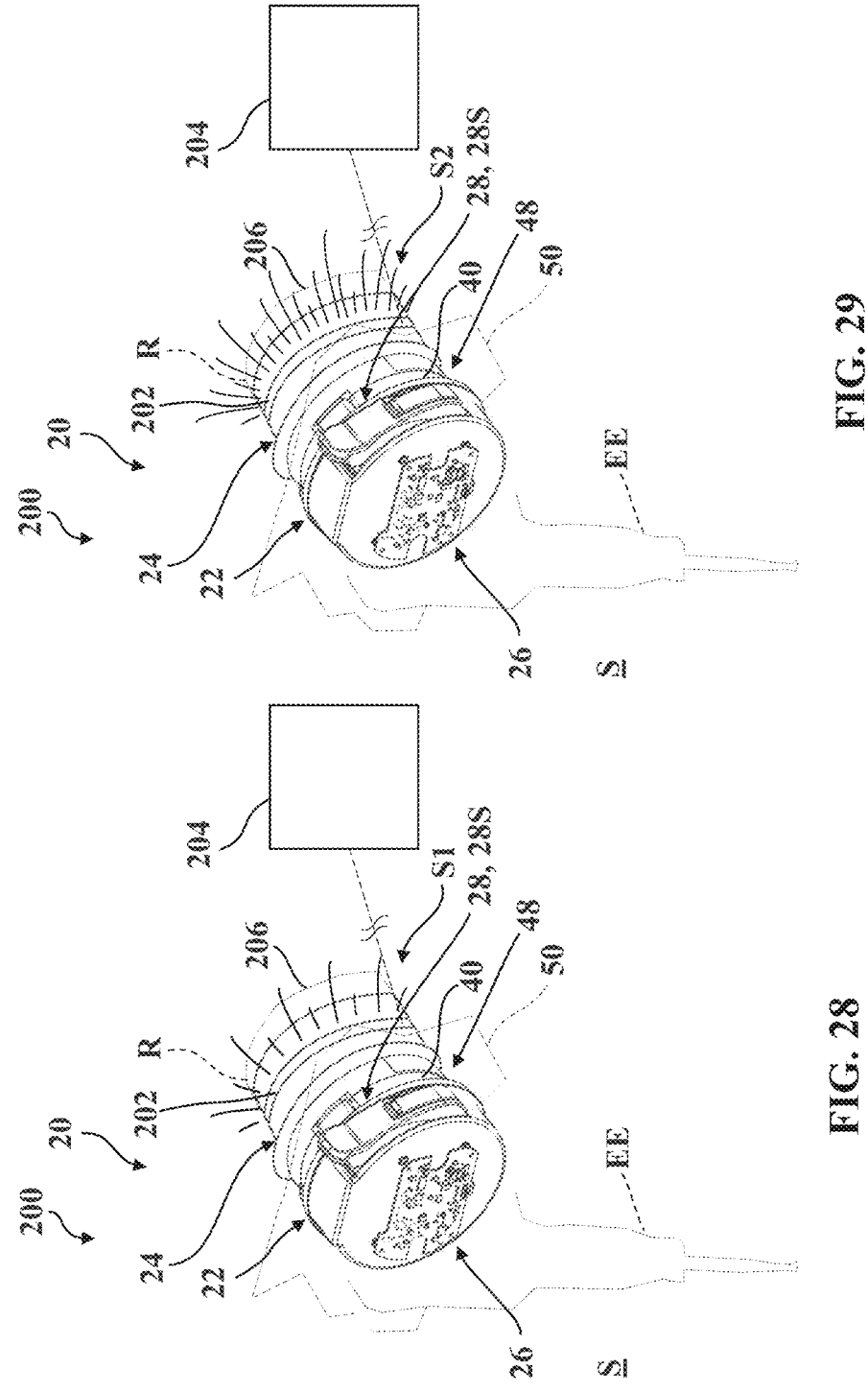
FIG. 28 is a perspective view of the robotic surgical system of FIG. 26 showing the illumination device in a first illumination state.
FIG. 29 is a perspective view of the robotic surgical system of FIG. 26 showing the illumination device in a second illumination state.

As shown in FIGS. 27-29, the illumination device 202 communicates with the controller 204 to change the light emission between at least the first and second illumination states S1, S2. The illuminated states provide visual feedback to the user that informs the user of the state of the robotic surgical system 200. The user interprets the light emission and reacts accordingly (e.g., by reinstalling improperly installed components of the mounting system, etc.).

Operation of the illumination device 202 may vary between conditions associated with the mounting system, as described below. In one example, one of the illumination states S1, S2 is indicative of an error state and another state S1, S2 is indicative of a proper state or a positive condition such as correct installation of a system component, or the like. The description herein does not necessarily limit any of the first or second states S1, S2 to be the designated error condition state, and hence, the terms "first" and "second" can be interchanged. The states S1, S2 may also be indicative of conditions unrelated to presence or absence of error. For example, the condition may be to communicate information to the user (e.g., confirmation before or after a user action). In one example, the first and second illumination states S1, S2 are "on/off" states, wherein the illumination device 202 emits light in one of the first and second illumination states S1, S2 and does not emit light in the other one of the first and second illumination states S1, S2. In another example, the illumination device 202 may flash in one or both of the first and second illumination states S1, S2. Moreover, when the illumination device 202 flashes in one or both of the first and second illumination states S1, S2, the speed at which the illumination device 202 flashes may vary between the first and second illumination states S1, S2 to differentiate between the states. In another example, the illumination device 202 emits light having a first color in the visible color spectrum in the first illumination state S1 and emits light having a second color in the visible color spectrum, different than the first color, in the second illumination state S2. In another example, the light emitted in the first and second illumination states S1, S2 may vary in brightness to differentiate between the first and second illumination states S1, S2.

The examples provided above are not mutually exclusive and may be utilized in conjunction with one another in any suitable arrangement (e.g., the illumination device 202 may flash the first color having a first brightness in the first illumination state S1, while the illumination device 202 may emit steady light in the second color having a second brightness (different from the second brightness) in the second illumination state S2). Moreover, the illumination device 202 may be configured to emit light in more than just the first and second illumination states S1, S2. In fact, the illumination device 202 may be configured to emit light in numerous illumination states to alert the user of many different conditions of the robotic surgical system 200.

In one example, the illumination device 202 is controlled to be in the first illumination state S1 when the end effector EE is coupled with the robotic arm R and controlled to be in the second illumination state S2 when the end effector EE is not coupled or improperly coupled with the robotic arm R. As such, the illumination device 202 in the second illumination state S2 would communicate to the user that the end effector EE is properly coupled to the robotic arm R and is in condition for operation. On the other hand, the illumination device 202 in the first illumination state S1 would communicate to the user that the end effector EE is not properly or improperly coupled to the robotic arm R and further manipulation of the end effector EE and the robotic arm R is needed to couple the end effector EE with the robotic arm R, e.g., to prevent inoperability or damage to the end effector EE and/or the robotic arm R. In some instances, the controller 204 may additionally permit operation of the end effector EE while the illumination device 202 is in the first illumination state S1, and the controller 204 may inhibit the operation of the end effector EE while the illumination device 202 is in the second illumination state S2.

In order to detect the coupling between the end effector EE and the robotic arm R, the controller 204 may communicate with the electronics of the first mounting portion 24. As described above, a sensor 140, such as but not limited to a Hall effect sensor (see FIG. 8) may be carried by the printed circuit board PCB fixed to the mounting hub 40. The corresponding magnet 142 (see FIG. 7) may be carried by the first hub 106 to rotate with the first hub 106. Alternatively, the sensor 140 may be carried by the first hub 106 to move relative to a magnet fixed on the printed circuit board PCB. As mentioned above, the sensor 140 is arranged to cooperate with the magnet 142 to generate signals indicative of the amount of rotation of the first hub 106 relative to the hub mount 40 and the first mounting plate 38. This provides the controller 204 (potentially including controller 144) with information about whether the second mounting portion 26 is appropriately secured to the first mounting portion 24 (i.e., hence ensuring proper coupling of the end effector EE with the robotic arm R). As such, the controller 204 wirelessly detects the coupling of the end effector EE with the robotic arm R. Other examples of the controller 204 wirelessly detecting the coupling between the end effector EE include, but are not limited to, inductive sensing and capacitive sensing.

Based on the sensor 140 signal (indicative of first hub 106 rotation), the controller 204 can control the illumination device 202 to be in the first state S1 when the controller 204 determines that the second mounting portion 26 is appropriately secured to the first mounting portion 24. On the other hand, the controller 204, 144 can control the illumination device 202 to be in the second state S2 when the controller 204, 144 determines that the second mounting portion 26 is not appropriately secured to the first mounting portion 24.

In another example, the sensor data can more generally detect proximity between the second mounting portion 26 and the first mounting portion 24. The controller 204, 144 can control the illumination device 202 to be in the first state S1 when the controller 204, 144 determines that the second mounting portion 26 not within a threshold proximity to the first mounting portion 24 and the controller 204, 144 can control the illumination device 202 to be in the second state S2 when the controller 204, 144 determines that the second mounting portion 26 is within a threshold proximity to the first mounting portion 24.

Alternatively, the coupling between the end effector EE and the robotic arm R may be detected through a direct electrical (wired) connection between the end effector EE and the robotic arm R. For example, as described above, the first mounting portion 24, the second mounting portion 26, and the sterile barrier assembly 22, can each employ one or more connectors, such as sealed electrical connectors, adapted to provide electrical connection between the first mounting portion 24 and the second mounting portion 26 to facilitate communication between the robotic arm R and the end effector EE. In the version shown in FIGS. 5B and 5C, first, second, and third connectors C1, C2, C3 are employed. However, different types of communication through the connectors C1, C2, C3 are contemplated without limitation. Furthermore, in other examples the electrical connection between the end effector EE and the robotic arm R may be accomplished without regard to the sterile barrier assembly 22.

Presence of a direct wired connection between electrical components in the mounting portions 24, 26 can be indicative of proper connection between the mounting portions 24, 26, whereas absence of the direct wired connection can be indicative of an improper connection between the mounting portions 24, 26. The controller 204 can control the illumination device 202 to be in the first state S1 when the controller 204 determines an absence of the direct wired connection between electrical components of mounting portions 24, 26 and can control the illumination device 202 to be in the second state S2 when the controller 204 determines a presence of the direct wired connection between electrical components of mounting portions 24, 26.

Alternatively, the connection between the mounting portions 24, 26 can be wired in both proper and improper installation conditions, but the controller 204 and/or any other sensor employed by the controller can detect electrical conditions (e.g., current, voltage, signal frequency/phase/amplitude, capacitance, impedance, etc.) to distinguish proper and improper installation. The controller 204, in such instances, can control the illumination device 202 accordingly.

Returning to FIGS. 28 and 29, in yet another example, the coupling between the end effector EE and the robotic arm R may be detected through actuation of a mechanical component, such as switch, button, trigger, or plunger, that electronically communicates with the controller 204. For example, as described above, the tensioner 28 of the second mounting portion 26 is movable between the first position 28F and second position 28S (as shown in FIGS. 2 and 3). The coupling 30 of the sterile barrier assembly 22 is configured to releasably secure to the first mounting portion 24 and to releasably receive the second mounting portion 26 when the tensioner 28 of the second mounting portion 26 is in the first position 28F. The kinematic couplers 32 are configured to engage the mounting portions 24, 26 and are arranged to provide a kinematic coupling between the mounting portions 24, 26 through the sterile barrier assembly 22 to constrain six degrees of freedom of movement between the surgical components when the tensioner 28 of the second mounting portion 26 is in the second position 28S. Here, the tensioner 28 position may be detected by any sensor (e.g., position sensor, proximity sensor, switch sensor) coupled to the controller 204. While the second mounting portion 26 is mounted to the sterile barrier assembly 22, the controller 204 can control the illumination device 202 to be in the first state S1 when the controller 204 determines that tensioner 28 is in the first position 28F, and the controller 204 can control the illumination device 202 to be in the second state S1 when the controller 204 determines that tensioner 28 is in the second position 28S.

In a related example, the illumination device 202 may be controlled to indicative an installation status of the sterile barrier assembly 22 relative to the first or second mounting portions 24, 26. In one example, a sensor (e.g., proximity, position, inertial, or force sensors) can be employed by the controller 204 to determine position or proximity of the sterile barrier assembly 22 to the first mounting portion 24. The sensor may be coupled to one or more of the sterile barrier assembly and the first mounting portion 24. From the sensor, the controller 204 can determine when the coupling 30 of the sterile barrier assembly 22 is properly secured to the first mounting portion 24 (with or without regard to the second mounting portion 26). Also, the controller 204, from the sensor, can determine when the coupling 30 of the sterile barrier assembly 22 is not properly secured (or not secured at all) to the first mounting portion 24. In such instances, the controller 204 can control the illumination device 202 to be in the first state S1 when the sterile barrier assembly 22 is properly secured to the first mounting portion 24 and control the illumination device 202 to be in the second state S2 when the sterile barrier assembly 22 is improperly or not secured to the first mounting portion 24.

For any examples above relating to controlling the illumination device 202 in regard to the mounting system, the illumination device 202 may further be controlled to any other illumination state to indicate a condition of the end effector EE and/or the robotic arm R before, during or after surgery. For example, the illumination device 202 may emit light in another illumination state when the end effector EE and/or the robotic arm R are operating properly or within suitable conditions. On the other hand, the illumination device 202 may emit light in another illumination state when the end effector EE and/or the robotic arm R are not operating properly or operating within unsuitable conditions (e.g., loss of accuracy, potential collision condition, etc.). Any other proper or error condition of the end effector EE and/or robotic arm R can be indicated by the illumination device 202.

Although many examples are provided above describing conditions of the robotic surgical system 200 that facilitate control of the illumination device 202, the list is not conclusive, and many other conditions may exist that correspond with alternating the light emitted by the illumination device 202.

Several examples have been discussed in the foregoing description. However, the examples discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:
1. A surgical system comprising:
a surgical robot comprising a robotic arm including a first mounting portion and an illumination device;
a sterile barrier assembly being releasably attachable to the first mounting portion;
a second mounting portion associated with a surgical component and being releasably attachable to the first mounting portion via the sterile barrier assembly, the second mounting portion comprising a tensioner movable from a first position to a second position to urge the second mounting portion towards the first mounting portion in response to movement of the tensioner towards the second position; and one or more controllers coupled to the illumination device and to one or more sensors and being configured to:

detect, using the one or more sensors, a first condition wherein the second mounting portion is attached to the first mounting portion via the sterile barrier assembly and the tensioner is in the first position;

control the illumination device to be in a first state to indicate the first condition;

detect, using the one or more sensors, a second condition wherein the second mounting portion is attached to the first mounting portion via the sterile barrier assembly and the tensioner is in the second position; and control the illumination device to be in a second state to indicate the second condition.

2. The surgical system of claim 1, wherein the surgical component is further defined as an end effector, the end effector comprising:

a housing for supporting an energy applicator; and the second mounting portion attached to the housing.

3. The surgical system of claim 1, wherein:

the sterile barrier assembly further comprises a coupling and a plurality of kinematic couplers; and the first mounting portion comprises:

a plurality of contact surfaces for engaging the plurality of kinematic couplers of the sterile barrier assembly;

a loading mechanism configured to apply a preload force to the second mounting portion through the sterile barrier assembly upon movement of the tensioner from the first position to the second position;

a first mounting plate and a first ball subassembly configured to releasably secure to the coupling of the sterile barrier assembly; and wherein the loading mechanism comprises a load actuator configured to move the first ball subassembly axially in response to movement of the tensioner towards the second position, wherein the load actuator comprises a first hub operatively attached to the first ball subassembly, a second hub operatively attached to the first mounting plate, and a plurality of ball bearings arranged between the first and second hubs, and ramps defined in one or more of the first and second hubs along which the ball bearings roll in response to movement of the tensioner towards the second position; and wherein the one or more controllers are configured to:

detect the first condition wherein the tensioner is in the first position by further detecting, using the one or more sensors, a first position or rotation amount of the first hub relative to the second hub; and detect the second condition wherein the tensioner is in the second position by further detecting, using the one or more sensors, a second position or rotation amount of the first hub relative to the second hub.

4. The surgical system of claim 1, wherein the one or more controllers are configured to:

detect the first condition wherein the tensioner is in the first position by further detecting, using the one or more sensors, a first position or movement of the tensioner; and detect the second condition wherein the tensioner is in the second position by further detecting, using the one or more sensors, a second position or movement of the tensioner.

5. The surgical system of claim 1, wherein:

the illumination device in the first state emits a first color; and the illumination device in the second state emits a second color different than the first color.

6. The surgical system of claim 1, wherein:

the illumination device is controlled to be inactive in the first state; and the illumination device is controlled to actively emit light in the second state.

7. The surgical system of claim 1, wherein the illumination device is disposed on the robotic arm adjacent to the first mounting portion.

8. The surgical system of claim 1, wherein the illumination device has an annular configuration encircling a link of the robotic arm.

9. The surgical system of claim 1, wherein the one or more controllers are further configured to detect, using the one or more sensors, installation of the sterile barrier assembly to the first mounting portion.

10. A method of operating a surgical system comprising a surgical robot comprising a robotic arm including a first mounting portion and an illumination device, a sterile barrier assembly being releasably attachable to the first mounting portion, a second mounting portion associated with a surgical component and being releasably attachable to the first mounting portion via the sterile barrier assembly, the second mounting portion comprising a tensioner movable from a first position to a second position to urge the second mounting portion towards the first mounting portion in response to movement of the tensioner towards the second position, and one or more controllers coupled to one or more sensors and the illumination device, the method comprising the one or more controllers:

detecting, using the one or more sensors, a first condition wherein the second mounting portion is attached to the first mounting portion via the sterile barrier assembly and the tensioner is in the first position;

controlling the illumination device to be in a first state to indicate the first condition;

detecting, using the one or more sensors, a second condition wherein the second mounting portion is attached to the first mounting portion via the sterile barrier assembly and the tensioner is in the second position; and controlling the illumination device to be in a second state to indicate the second condition.

11. The method of claim 10, wherein the sterile barrier assembly further comprises a coupling and a plurality of kinematic couplers, and the first mounting portion comprises: a plurality of contact surfaces for engaging the plurality of kinematic couplers of the sterile barrier assembly; a loading mechanism configured to apply a preload force to the second mounting portion through the sterile barrier assembly upon movement of the tensioner from the first position to the second position; a first mounting plate and a first ball subassembly configured to releasably secure to the coupling of the sterile barrier assembly; wherein the loading mechanism comprises a load actuator configured to move the first ball subassembly axially in response to movement of the tensioner towards the second position, wherein the load actuator comprises a first hub operatively attached to the first ball subassembly, a second hub operatively attached to the first mounting plate, and a plurality of ball bearings arranged between the first and second hubs, and ramps defined in one or more of the first and second hubs along which the ball bearings roll in response to movement of the tensioner towards the second position, the method comprising the one or more controllers further:

detecting the first condition wherein the tensioner is in the first position by further detecting, using the one or more sensors, a first position or rotation amount of the first hub relative to the second hub; and detecting the second condition wherein the tensioner is in the second position by further detecting, using the one or more sensors, a second position or rotation amount of the first hub relative to the second hub.

12. The method of claim 10, comprising the one or more controllers further:

detecting the first condition wherein the tensioner is in the first position by further detecting, using the one or more sensors, a first position or movement of the tensioner; and detecting the second condition wherein the tensioner is in the second position by further detecting, using the one or more sensors, a second position or movement of the tensioner.

13. The method of claim 10, comprising the one or more controllers further:

controlling the illumination device in the first state to emit a first color; and controlling the illumination device in the second state to emit a second color different than the first color.

14. The method of claim 10, comprising the one or more controllers further:

controlling the illumination device to be inactive in the first state; and controlling the illumination device to actively emit light in the second state.

15. The method of claim 10, comprising the one or more controllers further detecting, using the one or more sensors, the condition associated with installation of the sterile barrier assembly to the first mounting portion.

16. A surgical robotic system comprising:

a robotic arm comprising a plurality of links and joints and including a first mounting portion coupled to a distal end of the robotic arm, wherein the first mounting portion is configured to releasably receive a sterile barrier assembly and a second mounting portion associated with a surgical component, the second mounting portion being releasably attachable to the first mounting portion via the sterile barrier assembly, the second mounting portion comprising a tensioner movable from a first position to a second position to urge the second mounting portion towards the first mounting portion in response to movement of the tensioner towards the second position, and wherein the robotic arm comprises an illumination device; and one or more controllers coupled to the illumination device and to one or more sensors and configured to:

detect, using the one or more sensors, a first condition wherein the second mounting portion is attached to the first mounting portion via the sterile barrier assembly and the tensioner is in the first position;

control the illumination device to be in a first state to indicate the first condition;

detect, using the one or more sensors, a second condition wherein the second mounting portion is attached to the first mounting portion via the sterile barrier assembly and the tensioner is in the second position; and control the illumination device to be in a second state to indicate the second condition.

17. The surgical robotic system of claim 16, wherein the illumination device is disposed on the robotic arm adjacent to the first mounting portion and the illumination device has an annular configuration encircling one of the links of the robotic arm.

18. The surgical robotic system of claim 16, wherein the one or more controllers are configured to:

control the illumination device to emit a first color in the first state; and control the illumination device to be inactive, or to emit a second color different from the first color, in the second state.

* * * * *